(12) United States Patent
Osborne et al.

(10) Patent No.: US 10,927,408 B2
(45) Date of Patent: Feb. 23, 2021

(54) METHOD FOR EVALUATING MINORITY VARIANTS IN A SAMPLE

(71) Applicant: Personal Genome Diagnostics, Inc., Baltimore, MD (US)

(72) Inventors: Robert Osborne, Great Chesterford (GB); Esther Musgrave-Brown, Cambridge (GB)

(73) Assignee: Personal Genome Diagnostics, Inc., Baltimore, MD (US)

( * ) Notice: Subject to any disclaimer, the term of this patent is extended or adjusted under 35 U.S.C. 154(b) by 190 days.

(21) Appl. No.: 15/037,663

(22) PCT Filed: Nov. 26, 2014

(86) PCT No.: PCT/IB2014/003082
§ 371 (c)(1),
(2) Date: May 18, 2016

(87) PCT Pub. No.: WO2015/083004
PCT Pub. Date: Jun. 11, 2015

(65) Prior Publication Data
US 2016/0289753 A1    Oct. 6, 2016

Related U.S. Application Data

(60) Provisional application No. 61/910,890, filed on Dec. 2, 2013.

(51) Int. Cl.
*C12Q 1/6869* (2018.01)
*G16B 30/00* (2019.01)

(52) U.S. Cl.
CPC .......... *C12Q 1/6869* (2013.01); *G16B 30/00* (2019.02)

(58) Field of Classification Search
None
See application file for complete search history.

(56) References Cited

U.S. PATENT DOCUMENTS

| | | | |
|---|---|---|---|
| 8,133,667 B2 * | 3/2012 | Shapero | C12Q 1/683 435/6.12 |
| 8,685,678 B2 | 4/2014 | Casbon et al. | |
| 8,865,410 B2 | 10/2014 | Shendure et al. | |
| 9,260,753 B2 | 2/2016 | Xie et al. | |
| 2010/0069263 A1 * | 3/2010 | Shendure | C12N 15/1093 506/26 |
| 2011/0160078 A1 | 6/2011 | Foder et al. | |
| 2015/0361492 A1 | 12/2015 | Vogelstein et al. | |
| 2016/0215333 A1 | 7/2016 | Vogelstein et al. | |

FOREIGN PATENT DOCUMENTS

| | | |
|---|---|---|
| WO | WO2007037678 | 4/2007 |
| WO | WO2007073165 | 6/2007 |
| WO | WO 2009/152928 | 12/2009 |
| WO | WO2012142213 | 10/2012 |
| WO | WO 2012/159754 | 11/2012 |
| WO | WO2013123442 | 8/2013 |
| WO | WO2013128281 | 9/2013 |
| WO | WO2013130512 | 9/2013 |

OTHER PUBLICATIONS

Flaherty, P. et al. Ultrasensitive detection of rare mutations using net-generation targeted resequencing. Nucleic Acids Research, vol. 40 (1), p. e2 1-12, 2012.*
Amini, et al., "Haplotype-resolved whole genome sequencing by contiguity preserving transposition and combinatorial indexing", Nat Genet. 2014, 46(12): 1343-1349.
Hiatt, et al., "Parallel, tag-directed assembly of locally derived short sequence reads", Nat Methods, 2010, 7(2): 119-122.
Hiatt, et al., "Parallel, tag-directed assembly of locally derived short sequence reads; Supplementary figures and text", Nat Methods, 2010, 7(2): 119-122.
Hoang, et al., "Genome-wide quantification of rare somatic mutations in normal human tissue using massively parallel sequencing", Proc Natl Acad Sci U S A., 2016, 113: 9846-51.
Casbon, et al. "A method for counting PCR template molecules with application to next-generation sequencing", Nucleic Acids Research, 2011, vol. 39, No. 12, e81, pp. 1-8.
Gundry, et al., "Direct mutation analysis by high-throughput sequencing: from germline to low-abundant, somatic variants", Mutat Res., 2012, 729(1-2): 1-15.
Flaherty, et al., "Ultrasensitive detection of rare mutations using next-generation targeted resequencing", Nucleic Acids Research, 2012, 40(1): 1-12.
Kinde, et al. "Detection and quantification of rare mutations with massively parallel sequencing", Proceedings of the National Academy of Sciences USA, vol. 108, No. 23, 2011, pp. 9530-9535.
Kivioja, et al. "Counting absolute numbers of molecules using unique molecular identifiers", Nature Methods, vol. 9, No. 1, 2012, pp. 72-74.

* cited by examiner

*Primary Examiner* — Young J Kim
(74) *Attorney, Agent, or Firm* — Scully, Scott, Murphy & Presser, P.C.

(57) ABSTRACT

A method of evaluating a sequence variation in a sample is provided. In some embodiments, the method may involve: amplifying a nucleic acid product from an initial sample; fragmenting an amount of the nucleic acid product to produce fragments; attaching an adaptor to each end of the fragments to produce adaptor-tagged fragments; sampling no more than 10% of the tagged fragments and amplifying them; sequencing at least some of the copies of the fragments to produce a plurality of sequence reads; grouping sequence reads for copies of fragments that have the same fragmentation breakpoints; deriving a consensus sequence for each of the read groups; and aligning the consensus sequences with a reference sequence.

21 Claims, 11 Drawing Sheets
Specification includes a Sequence Listing.

After the reads are grouped, a consensus sequence for each of the groups is generated (this step could include use of quality metrics or simply counting the bases at each position).

An example read-group with errors underlined.

AGAGA<u>G</u>AGATATAGAGAGACACAG
AGAGACAGAT<u>C</u>TAGAGAGACACAG
AGAGACAGATATAGAGAG<u>A</u>ACAG
AGAGACAGATATAGAGAG<u>A</u>ACAG
AGAGACAGATATAGAGAG<u>A</u>ACAG
AGAGACAGATATAGAGAGACACAG

↓

For example, a consensus generated using read counts.

AGAGACAGATATAGAGAGANACAG
     ↑    ↑        ↑

1G:5C  1C:5A    3A:3C
Call C  Call A    Unknown
                      Call N

FIG. 3

1) Generate PCR amplicons then randomly fragment:
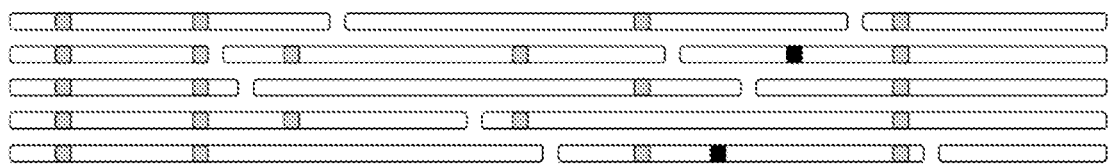
2) Dilute:
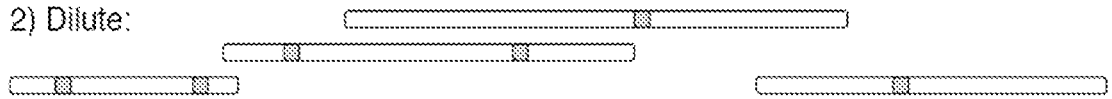
3) Limited cycle PCR:
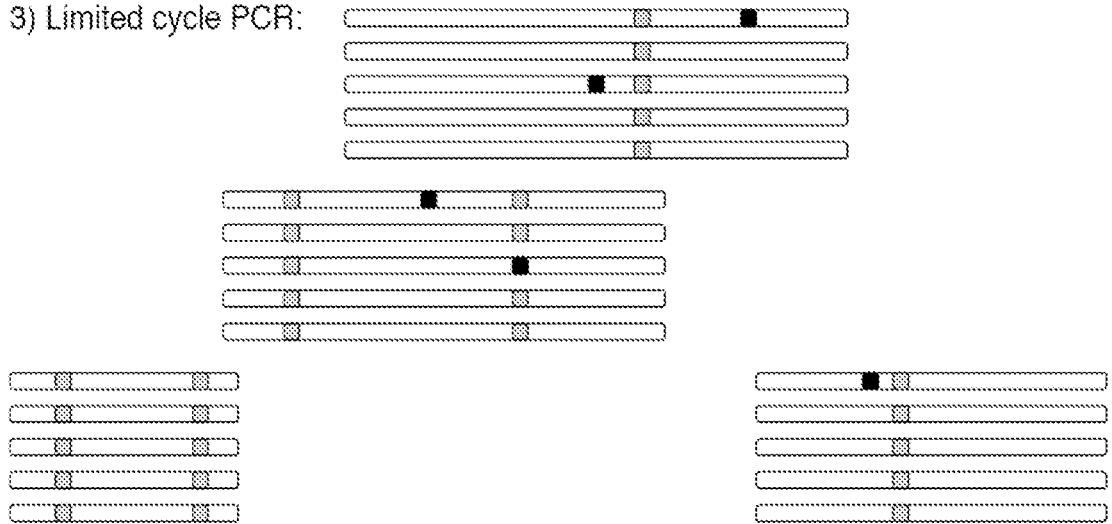
FIG. 4

4) Sequence a subset of the amplicons:
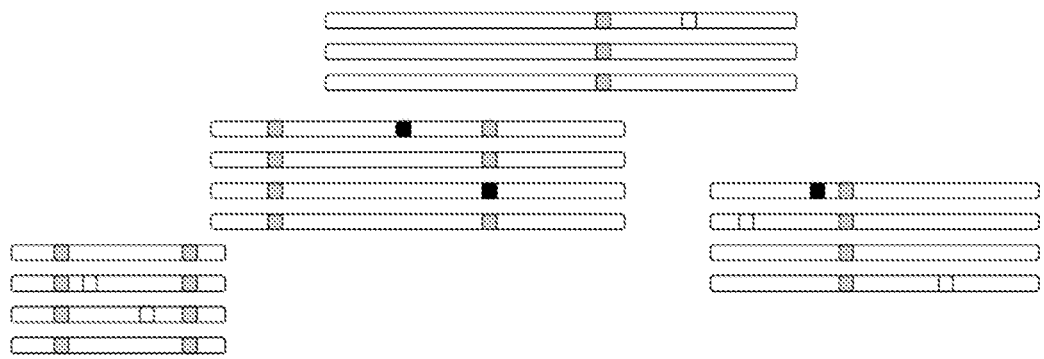
5) Generate consensus reads with PCR and sequencing errors removed:
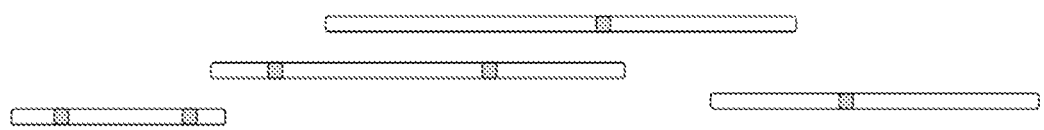
6) Align with reference sequence and identify variants:
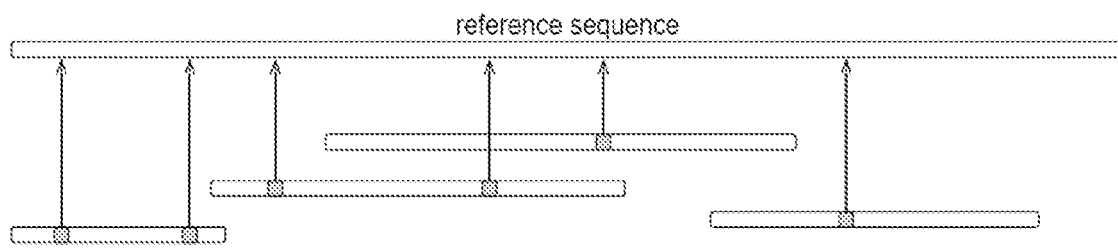
Key: genuine variants  ■ PCR error  □ sequencing error
FIG. 4 (continued)

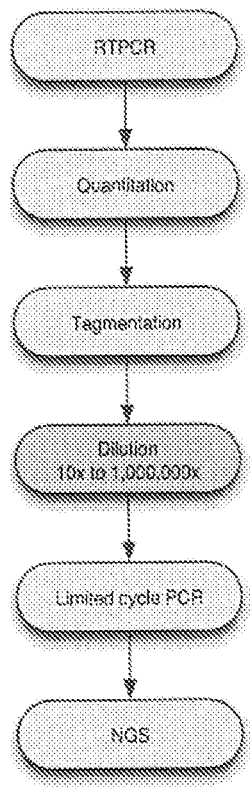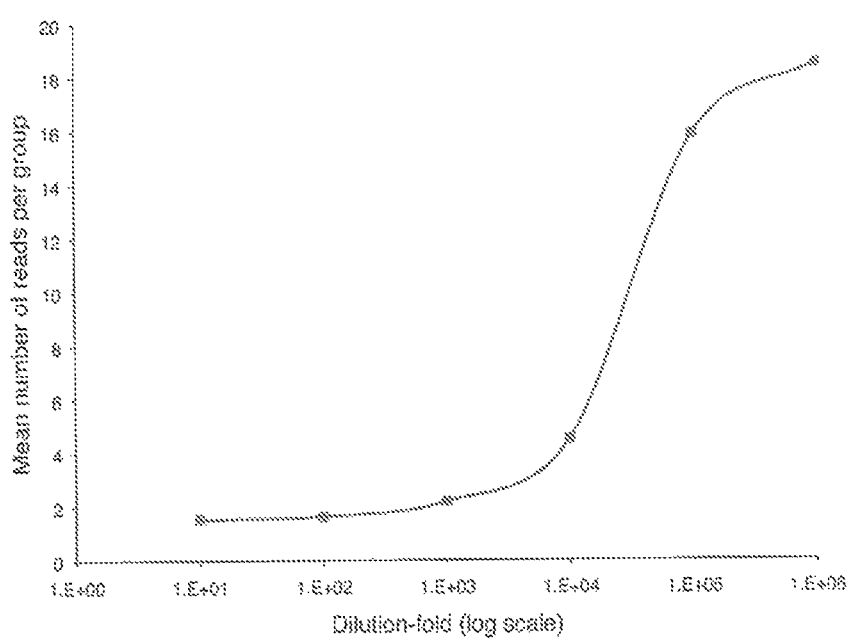
FIG. 5

Standard Nextera post-fragmentation workflow:
'Tagmentation' reaction product:
• Add PCR primers containing sample indexes and MiSeq sequences:
• Run a limited cycle PCR to produce a sequencer-ready, indexed amplicon:
▨ ▨ ☐ Nextera transposase sequences
▨ Illumina MiSeq sequences
FIG. 6

Adapted to incorporate VeriTags:

- 'Tagmentation' reaction product:

- Add PCR primers containing sample indexes and MiSeq sequences and a 3' blocked oligo containing a VeriTag:

- Run the first PCR cycle with a 55°C annealing temp to copy the VeriTag into the top strand...

...the bottom strand is copied too but the VeriTag is not incorporated:

- Run subsequent cycles with a 72°C annealing temp to prevent further VeriTag incorporation into bottom strand copies and produce a sequencer-ready, indexed and VeriTagged amplicon:

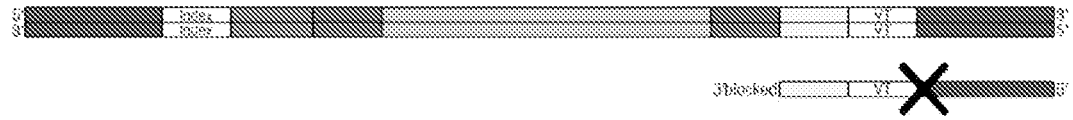

FIG. 6 (continued)

```
                        SEQUENCE LISTING

<160> NUMBER OF SEQ ID NOS: 7

<210> SEQ ID NO 1
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 1
agagagagat atagagagac acag                                            24

<210> SEQ ID NO 2
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 2
agagacagat ctagagagac acag                                            24

<210> SEQ ID NO 3
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 3
agagacagat atagagagaa acag                                            24

<210> SEQ ID NO 4
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 4
agagacagat atagagagaa acag                                            24

<210> SEQ ID NO 5
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 5
agagacagat atagagagaa acag                                            24

<210> SEQ ID NO 6
<211> LENGTH: 24
<212> TYPE: DNA
```

```
<213> ORGANISM: Artificial Sequence
<220> FEATURE:
<223> OTHER INFORMATION: Synthetic oligonucleotide

<400> SEQUENCE: 6
agagacagat atagagagac acag                                              24

<210> SEQ ID NO 7
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (20)..(20)
<223> OTHER INFORMATION: n is a, c, g, or t

<400> SEQUENCE: 7
agagacagat atagagagan acag                                              24
```

METHOD FOR EVALUATING MINORITY VARIANTS IN A SAMPLE

CROSS-REFERENCING

This patent application claims the benefit of U.S. provisional application Ser. No. 61/910,890, filed on Dec. 2, 2013, which patent application is incorporated by reference herein in its entirety.

BACKGROUND

So called "next generation" sequencing platforms have the potential to provide an unprecedented insight into how pathogen genomes evolve during an infection (see, e.g., Archer et al, PLoS Comput Biol 2010, 6:e1001022; Poon et al, Mol Biol Evol 2009, 27:819-832, among others). Within chronic viral infections, such as HIV-1 and HCV, the study of variation is important as it has been directly associated with both disease progression and the outcome of treatment (see, e.g., Bosch et al, J Mol Diagn 2008, 10:484-492; Lal et al, Indian J Med Res 2005, 121:287-314; and Tazi et al, BMC Evol Biol 2011, 11:62).

Next generation sequencing has the potential to accurately identify and quantify the sites of nucleic acid sequence variation within the genomes of viral populations present in a host. In particular, it is very desirable to quantify the variation in viral populations that have been sampled from the host through time, or from differing compartments in the host, thereby providing a detailed picture of viral evolution during an infection. Knowledge of the variation in viral genomes that occurs during an infection has several applications, including for the development of treatment strategies that are both reactive (in that information can be used to select the best drug treatment regime for an individual patient) and predictive (in that the likelihood of the emergence of resistant variants can be calculated and incorporated into vaccine design strategies). However, before next generation sequencing technology can be used routinely to characterize patterns of variation, problems need to be addressed. The major problem involves the detection of errors introduced during sequencing and distinguishing those errors from real genetic variation. This problem is particularly acute for RNA viruses such as HIV-1 because the degree of genetic variation may be on the same order as the error rate of the sequencer.

All sequencing methods inherently produce errors that are generated by, e.g., mis-calling a base (where the sequence-processing software calls a base incorrectly), or amplification (where the polymerase incorporates a non-complementary base during production of the sequencing library or during the sequencing reaction itself). These problems limit one's ability to identify true sequence variation in the sample and, indeed, because of these problems many of the current methods are reported to have a low specificity or a high false positive rate. For example, Quail et al (A tale of three next generation sequencing platforms: comparison of Ion Torrent, Pacific Biosciences and Illumina MiSeq sequencers Michael A Quail*, Miriam Smith, Paul Coupland, Thomas D Otto, Simon R Harris, Thomas R Connor, Anna Bertoni, Harold P Swerdlow and Yong Gu BMC Genomics. 2012 Jul. 24; 13:341. doi: 10.1186/1471-2164-13-341) calculated raw error rates for Ion Torrent PGM and Illumina MiSeq sequencers at 1.71% and 0.8%. The percentage of error-free reads, without a single mismatch or indel, was 76.45% for MiSeq and 15.92% for Ion Torrent. Against this background, it is difficult to detect low frequency variants with high specificity and sensitivity.

One method to increase the specificity of detection for low frequency genetic variants is to apply molecule identifier sequences as described in Casbon et al (Nuc. Acids Res. 2011, 22 e81) as well as U.S. Pat. Nos. 8,481,292, 8,685,678, 8,722,368, 8,728,766, and 8,715,967, which are incorporated herein by reference. However, RNA viruses such as HIV-1 and HCV present specific challenges for molecule identifier sequence analysis due to the high diversity of viral sequences and the wide range of viral titers.

The main (M) group of HIV-1 includes nine major subtypes (A-D, F-H, J and K), four sub-subtypes (A1 and A2, F1 and F2) and over 55 circulating recombinant forms. HCV has eleven genotypes (1-11), each comprised of multiple subtypes (for example, 1a and 1b). The level of diversity makes it difficult to design primers capable of reliably amplifying viruses across different genotypes and subtypes. Further, the typical read length for many sequencing platforms is much shorter than the fragments generated by the "best" PCR primers. This primer design constraint has led some researchers to amplify only relative small segments of a viral genome, which is sub-optimal for a variety of reasons, not least of which is that the primers may not amplify all genotypes or capture all of the important sites of potential variation. Longer amplicons are preferred as fewer primers are required and thus there is greater flexibility with respect to the genomic positions of the primers. Unfortunately, in some instances molecule identifier sequences cannot be adapted easily to use with longer amplicons because the sequence reads do not cover the entire amplicon.

In addition, molecule identifier sequences can be sensitive to the number of template molecules. The use of molecule identifier sequences relies on the efficient distribution of raw sequencing reads across different identifier sequences. A major determinant of the number of reads in associated with each identifier sequence is the number of input molecules into the molecule identifier sequence tagging reaction. Too many input molecules result in identifier sequences that are associated with too few reads to enable error-correction. In contrast, too few input molecules results in identifiers that are associated with more reads than is necessary for error-correction, thereby wasting sequencing reads. In some cases viral titers can range across a wide dynamic from one clinical sample to the next or during the course of the infection. For example, HIV-1 quantitative RT-PCR assays are designed for widely varying viral loads of between 40 and $10^7$ copies/mL (Abbott, Roche). Similarly, HCV quantitative RT-PCR assays are designed for viral loads between 12 and $10^8$ IU/mL (Abbott) (IUs are international units, a calibrated WHO HCV RNA standard).

In an alternative method, RT-PCR amplicons could be fragmented after RT or after limited RT-PCR cycles. However, this method is practically difficult to implement because: (1) many sequencing methods (particularly those that use transposable elements or physical methods to fragment the initial sample) require a minimal amount of input DNA; (2) contaminating host DNA can be fragmented and tagged and result in wasted sequencing reads; (3) fragmentation methods are not reliable on samples with low template mass (such as unamplified samples or samples with limited amplification cycles). For example, the commercial Nextera XT (Illumina) fragmentation and labeling system requires 1 ng of input mass. This is equivalent to about 330 different copies of a haploid human genome or, for a much smaller genome of 10 kb~108,900,000 double-stranded DNA molecules.

In view of the above, there is still an acute need for methods that accurately identify and, optionally, quantify sequence variations in a sample with high specificity and sensitivity on longer amplicons.

SUMMARY

Described below is a workflow that that enables the accurate and sensitive determination of low levels of sequence variation in the nucleic acids in sample, even if a wide range of concentration in these samples exists. The principles of the method are described in the context of the analysis of a viral genome, e.g., HIV or HCV. However, the general principle of the method can be applied to other samples where low levels of sequence variation exist, e.g., in the analysis of bacterial genomes (where the sequence variation may provide resistance to an antibiotic) or in the analysis of the human genome (where a sample may contain a relatively low amount of a mutated gene).

In certain embodiments, the method comprises:

a) amplifying a nucleic acid product from an initial sample;

b) fragmenting an amount of the nucleic acid product produced by step a) to produce fragments;

c) attaching an adaptor to each end of the fragments created in step b) to produce adaptor-tagged fragments d) sampling no more than 10% of the product of step c) and amplifying the adaptor-tagged fragments contained in the sampled product using one or more primers that hybridize to the adaptor to produce copies of the fragments e) sequencing at least some of the copies of the fragments produced in d) to produce a plurality of sequence reads;

f) computationally grouping sequence reads for copies of fragments that have the same fragmentation breakpoints and substantially identical sequences to produce read groups;

g) deriving a consensus sequence for each of the read groups;

h) aligning the consensus sequences with a reference sequence; and i) identifying a position in the alignment that comprises a sequence variation.

Depending on how the method is implemented, the method may have certain advantages over the conventional methods.

Firstly, the initial amplification step (which may be done by RT-PCR in some cases) can be employed (without the need to quantify the template concentration) to effectively normalize the mass of nucleic acid used in downstream steps (e.g., fragmentation), thereby addressing the problems associated with sample-to-sample input mass variation. Thus, the method can be used on samples that have a very wide variation in the concentration of the target nucleic acids, and can be used on samples in which the target nucleic acids are at an unknown concentration. Further, the initial amplification step can be tailored to provide relatively long products, which avoids the problems caused by the target sequences being very diverse by providing much more flexibility for positioning amplification primers while also addressing issues generated by amplifying several short segments (reducing the number of reactions or the need to multiplex).

The fragmentation step of the method, in combination with the second amplification step (in which the product of step b is "sampled" and amplified) allows one to group sequences that have the same fragmentation breakpoints. This, in turn, allows consensus sequences to be generated and, using consensus sequences generated from the sequence reads, errors and biases that result from amplification or sequencing steps can be eliminated. The consensus sequence approach eliminates significantly more errors than conventional methods, which often just analyze the "best" sequences.

Finally, the number of sequence reads that are used to assemble each consensus sequence can be tuned to a level that provides a desired specificity and error rate. For example, if one wanted a very low error rate, one might specify at least 20× sequence reads per consensus sequence. For a different application, one might require a less stringent error threshold and therefore specify 3× reads per read-group. Because the mixture of molecules produced after fragmentation is highly complex (there may be millions, if not tens of billions of different molecules) and most sequencing platforms are only capable of providing a limited number of sequence reads in a single run, it is often desirable to amplify a tiny fraction of the fragmented sample, thereby allowing several sequencing reads per fragment (where each read corresponds to a copy of the fragment). This "sampling" step runs contrary to current thinking (in which PCR duplicates are removed as part of bioinformatic analysis).

Other variations on this workflow enable the analysis of samples from more than one biological source of interest (e.g., multiple patients, multiple samples from the same patient, etc.). In one exemplary method, this is done by processing each sample in parallel up to step (c) above, then modifying step (d) so that a sample identifier sequence (also known as a Multiplex Identifier or MID) is introduced, then pooling samples together before the sequencing step and, during the sequence analysis steps, segregating the sequences associated with each unique sample so that a meaningful result for each individual sample in the pool is obtained. In another exemplary method, one could add the sample identifier sequence as part of the adaptors in step (c) and then pool samples together before the remaining steps in the workflow. The pooling can be done at any step after sample identifier sequences have been added e.g. in step c). As would be apparent, steps b) and c) can be done in a single reaction if a transposable element system is used.

BRIEF DESCRIPTION OF THE FIGURES

The skilled artisan will understand that the drawings, described below, are for illustration purposes only. The drawings are not intended to limit the scope of the present teachings in any way.

FIG. 3 shows a read group and how a consensus sequence can be made. From top to bottom: SEQ ID NOS 1-7.

FIG. 4 schematically illustrates some of the general principles of the present method.

FIG. 5 is a graph showing that a higher dilution results an increase in the mean number of reads per read group in the context of the present method.

FIG. 6 shows one way in which molecule identifier sequences (called "VeriTags" in the figure), can be incorporated into the Nextera workflow. In this method (shown on the right) the oligonucleotides are designed in such a way that the molecule identifier sequences become attached to subsequently generated amplicons only at low temperature.

DEFINITIONS

Figure 1:
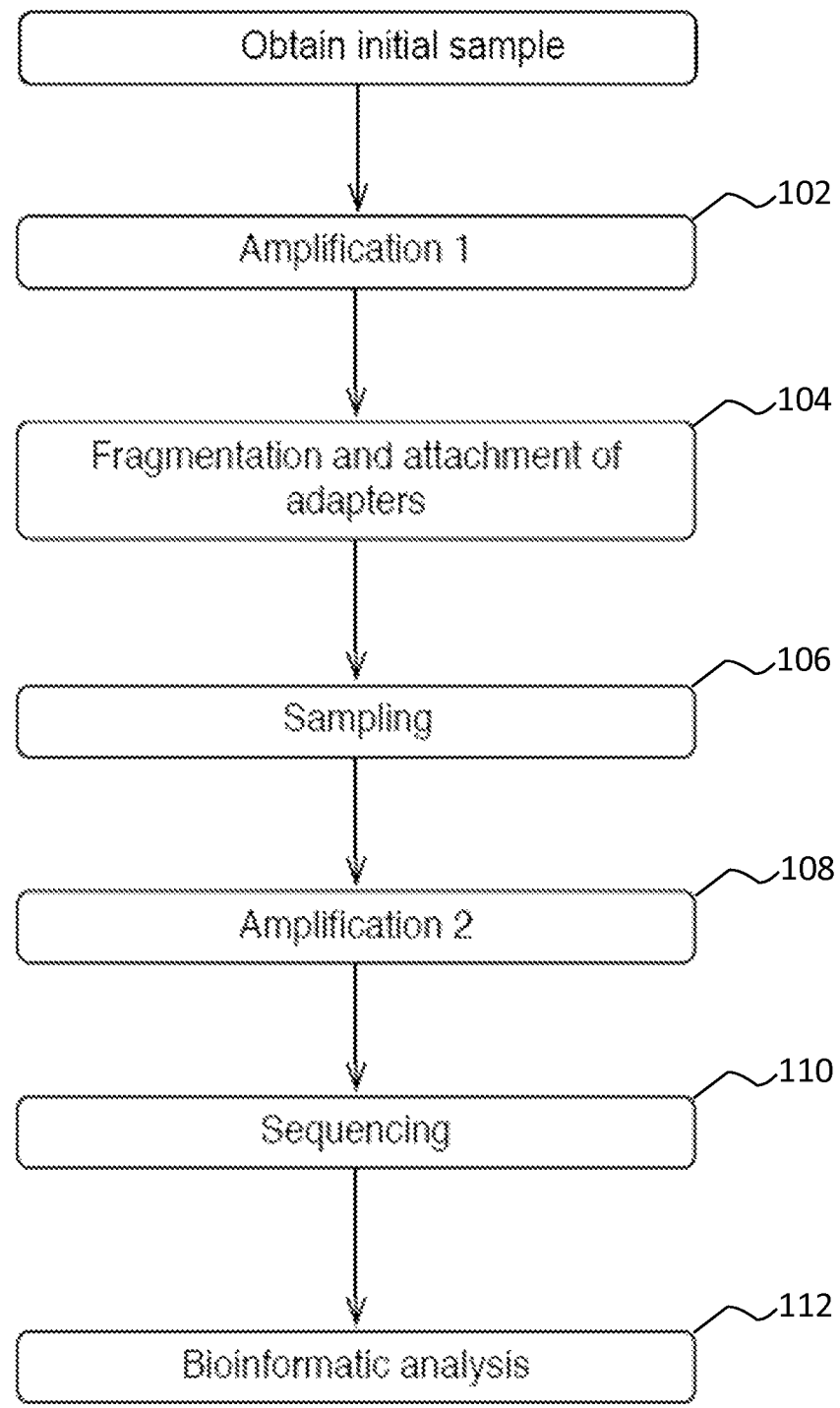
FIG. 1 is a flow-chart showing some of the sample processing steps of one implementation of the present method.

Unless otherwise defined, all technical and scientific terms used herein have the same meaning as commonly understood by one of ordinary skill in the art to which this invention belongs. Still, certain elements are defined for the sake of clarity and ease of reference.

Terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

"Amplicon" means the product of a polynucleotide amplification reaction. That is, it is a population of polynucleotides, usually double stranded, that are replicated from one or more starting sequences. The one or more starting sequences may be one or more copies of the same sequence, or it may be a mixture of different sequences. Amplicons may be produced by a variety of amplification reactions whose products are multiple replicates of one or more target nucleic acids. Generally, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683,195; 4,965,188; 4,683,202; 4,800,159 (PCR); Gelfand et al, U.S. Pat. No. 5,210,015 (real-time PCR with "TAQMANT™" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-2155 (1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like.

"Genetic locus," "locus,", "locus of interest", "region" or "segment" in reference to a genome or target polynucleotide, means a contiguous sub-region or segment of the genome or target polynucleotide. As used herein, genetic locus, locus, or locus of interest may refer to the position of a nucleotide, a gene or a portion of a gene in a genome, including mitochondrial DNA or other non-chromosomal DNA (e.g., bacterial plasmid), or it may refer to any contiguous portion of genomic sequence whether or not it is within, or associated with, a gene. A genetic locus, locus, or locus of interest can be from a single nucleotide to a segment of a few hundred or a few thousand nucleotides in length or more. In general, a locus of interest will have a reference sequence associated with it (see description of "reference sequence" below).

The terms "plurality", "population" and "collection" are used interchangeably to refer to something that contains at least 2 members. In certain cases, a plurality, population or collection may have at least 10, at least 100, at least 1,000, at least 10,000, at least 100,000, at least $10^6$, at least $10^7$, at least $10^8$ or at least $10^9$ or more members.

The term "adaptor" refers a sequence that is added (e.g., by ligation) to a nucleic acid. An adaptor may be from 5 to 100 bases in length, and may provide, e.g., an amplification primer binding site, a sequencing primer binding site, and/or a molecular identifier such as a sample identifier sequence or molecule identifier sequence. An adaptor may be added to the 5' end, the 3' end, or both ends of nucleic acid molecule. A double stranded adaptor can be added to a fragment by ligating only one strand of the adaptor to the fragment. The sequence of the non-ligated strand of the adaptor may be added to the fragment using a polymerase. An adaptor can also be added by primer extension when the primer comprises, at its 3' end, a sequence that binds to the target region of interest and at its 5' end sequence elements, such as primer binding sites, that may be utilized in subsequent biochemical manipulations or analysis of the adaptor-labeled sample.

The term "sample identifier sequence", "sample index", "multiplex identifier" or "MID" is a sequence of nucleotides that is appended to a target polynucleotide, where the sequence identifies the source of the target polynucleotide (i.e., the sample from which sample the target polynucleotide is derived). In use, each sample is tagged with a different sample identifier sequence (e.g., one sequence is appended to each sample, where the different samples are appended to different sequences), and the tagged samples are pooled. After the pooled sample is sequenced, the sample identifier sequence can be used to identify the source of the sequences. A sample identifier sequence may be added to the 5' end of a polynucleotide or the 3' end of a polynucleotide. In certain cases some of the sample identifier sequence may be at the 5' end of a polynucleotide and the remainder of the sample identifier sequence may be at the 3' end of the polynucleotide. When elements of the sample identifier has sequence at each end, together, the 3' and 5' sample identifier sequences identify the sample. In many examples, the sample identifier sequence is only a subset of the bases which are appended to a target oligonucleotide.

The term "molecule identifier sequence" (which may also be referred to as a "counter sequence", or "VeriTag" in some instances) is a sequence of nucleotides that can be appended to the nucleic acid fragments of a sample such that the appended sequence of nucleotides, alone or in combination with other features of the fragments, e.g., their fragmentation breakpoints, can be used to distinguish between the different fragment molecules in the sample or a portion thereof. The complexity of a population of molecule identifier sequences used in any one implementation may vary depending on a variety of parameters, e.g., the number of fragments in a sample and/or the amount of the sample that is used in a subsequent step. For example, in certain cases, the molecule identifier sequence may be of low complexity (e.g., may be composed of a mixture of 8 to 1024 sequences). In other cases, the molecule identifier sequence may be of high complexity (e.g., may be composed of 1025 to 1M or more sequences). In certain embodiments, a population of molecule identifier sequences may comprise a degenerate base region (DBR) comprising one or more (e.g., at least 2, at least 3, at least 4, at least 5, or 5 to 30 or more) nucleotides selected from R, Y, S, W, K, M, B, D, H, V, N (as defined by the IUPAC code), or a variant thereof. As described in U.S. Pat. No. 8,741,606, a molecule identifier sequence may be made up of sequences that are non-adjacent. In some embodiments, a population of molecule identifier sequences may by made by mixing oligonucleotides of a defined sequence together. In these embodiments, the molecule identifier sequence in each of the oligonucleotides may be error correcting. In the methods described herein, the molecule identifier sequence may be used to distinguish between the different fragments in a portion of an initial sample, where the portion has been removed from the initial sample. The molecule identifier sequences may be used in conjunction with other features of the fragments (e.g., the end sequences of the fragments, which define the breakpoints) to distinguish between the fragments.

The term "variable", in the context of two or more nucleic acid sequences that are variable, refers to two or more nucleic acids that have different sequences of nucleotides relative to one another. In other words, if the polynucleotides of a population have a variable sequence, then the nucleotide sequence of the polynucleotide molecules of the population varies from molecule to molecule. The term "variable" is not to be read to require that every molecule in a population has a different sequence to the other molecules in a population.

The term "substantially" refers to sequences that are near-duplicates as measured by a similarity function, including but not limited to a Hamming distance, Levenshtein distance, Jaccard distance, cosine distance etc. (see, generally, Kemena et al, Bioinformatics 2009 25: 2455-65). The exact threshold depends on the error rate of the sample preparation and sequencing used to perform the analysis, with higher error rates requiring lower thresholds of similarity. In certain cases, substantially identical sequences have at least 98% or at least 99% sequence identity.

The term "consensus" refers to a sequence that is obtained by aligning a set of reads over a specific genomic region or regions and is defined as the most likely sequence that represents the predominant base at each position in the reads. Methods for obtaining a consensus sequence are known (see e.g., US20120330566, which is incorporated by reference).

The term "sampling" is intended to refer to an action in which a relatively minor portion of an product is used in the next step of a protocol. Sampling requires removal of a small portion of the volume of the product and, in certain cases, may involve diluting the product (into, e.g., a larger volume) and then removing a portion of the diluted product (e.g., 0.5 µl to 10 µl) for use in the next step of the method. The term "sampling" is intended to mean that all the molecules in a volume of the product are removed from the product without regard to the sequences of the removed molecules. The term "fragmenting" includes methods in which sites are cleaved in a substantially non-sequence-specific way. Such substantially non-sequence-specific methods include physical fragmentation methods such as nebulization, sonication and shearing, chemical methods, as well as transposase-mediated methods (see, e.g., Caruccio, Methods Mol Biol. 2011; 733:241-55) and other fragmentation methods that use restriction enzymes and other nucleases that cleave DNA or have been engineered to cleave DNA in a random or semi-random way. In certain applications, fragmentation may include methods where the fragmentation is not random or semi-random.

The term "fragmentation breakpoint" is intended to refer to the site at which a nucleic acid is cleaved to produce a fragment. Two fragments that have the same fragmentation breakpoints have the same sequences at their ends (excluding any adaptor sequences that have been added to the fragments). Fragmentation breakpoints can be generated by random or non-random methods.

The terms "minority variant" and "sequence variation" are defined as a variant that is present a frequency of less than 20%, relative to other molecules in the sample. In some cases, a minority variant may be a first allele of a polymorphic target sequence, where, in a sample, the ratio of molecules that contain the first allele of the polymorphic target sequence compared to molecules that contain other alleles of the polymorphic target sequence is 1:100 or less, 1:1,000 or less, 1:10,000 or less, 1:100,000 or less or 1:1,000,000 or less. Minority variants of drug resistant HIV are described in Gianella et al (J Infect Dis. (2010) 202: 657-666). A variant can be a substitution, insertion, deletion, inversion, duplication, conversion, translocation or complex event where more than one of these processes has occurred.

The term "HIV" refers to human immunodeficiency virus. HIV can be divided into two major types, HIV type 1 (HIV-1) and HIV type 2 (HIV-2). HIV-1 is the most common and pathogenic strain of the virus. Scientists divide HIV-1 into a major group (Group M) and several minor groups. With 'M' for "major", this is by far the most common type of HIV, with more than 90% of HIV/AIDS cases deriving from infection with HIV-1 group M. The M group is subdivided further into clades, called subtypes, that are also given a letter. There are also "circulating recombinant forms" or CRFs derived from recombination between viruses of different subtypes which are each given a number. CRF12_BF, for example, is a recombination between subtypes B and F.

The term "defined amount" may be measured in moles, weight or volume if a volume contains a known concentration of nucleic acid. The concentration of nucleic acid in a sample can be determined using any suitable method.

The term "amplifying" is intended to refer to both isothermal amplification methods and methods that require thermocycling (e.g., PCR). Amplification requires increasing the relative concentration of one or more sequences in a sample at least 10-fold, relative to unamplified components of the sample.

The term "nucleic acid template" is intended to refer to the initial nucleic acid molecule that is copied during amplification. Copying in this context can include the formation of the complement of a particular single-stranded nucleic acid. The "initial" nucleic acid can comprise nucleic acids that have already been processed, e.g., amplified, extended, labeled with adaptors, etc.

The term "tailed", in the context of a tailed primer or a primer that has a 5' tail, refers to a primer that has a region (e.g., a region of at least 12-50 nucleotides) at its 5' end that does not hybridize or partially hybridizes to the same target as the 3' end of the primer.

The term "initial template" refers to a sample that contains a target sequence to be amplified.

The term "attaching an adaptor" comprises the act of ligating or otherwise adding an adaptor to a fragment. A double stranded adaptor can be ligated to an adaptor by both strands of the adaptor or by one strand of the adaptor. An adaptor can also be added by primer extension when the primer comprises, at its 3' end, a sequence that binds to the target region of interest and at its 5' end sequence elements, such as primer binding sites, that may be utilized in subsequent biochemical manipulations or analysis of the adaptor-labeled sample.

The term "next generation sequencing" refers to the so-called highly parallelized methods of performing nucleic acid sequencing and comprises the sequencing-by-synthesis or sequencing-by-ligation platforms currently employed by Illumina, Life Technologies, Pacific Biosciences and Roche, etc. Next generation sequencing methods may also include, but not be limited to, nanopore sequencing methods such as offered by Oxford Nanopore or electronic detection-based methods such as the Ion Torrent technology commercialized by Life Technologies.

The term "sequence read" refers to the output of a sequencer. A sequence read typically contains a string of Gs, As, Ts and Cs, of 50-1000 or more bases in length and, in many cases, each base of a sequence read may be associated with a score indicating the quality of the base call.

The term "read group" refers to a group of sequence reads that have the same fragmentation breakpoints and substantially identical sequences. A read group is not a "contig". Rather, a read group is a collection of sequences that are almost identical to one another and that have the same start and end points, where the terms "substantially identical" and "almost identical" are intended to accommodate the expected sequence variation generated by sequencing errors, amplification (PCR) errors, and the level of mutations in the sample being sequenced.

The term "copies of fragments" refers to the product of amplification, where a copy of a fragment can be a reverse complement of a strand of a fragment, or have the same sequence as a strand of a fragment.

The term "substantially identical sequences" refers to sequence that are at least 95% or at least 99% identical to one another.

The term "counting" refers to any way of determining or assessing the number of something.

The term "the number of consensus sequences having a sequence variation" and grammatical equivalents thereof refer to the number of consensus sequences that contain the nucleotide sequence of a particular sequence variant. For example, if two consensus sequences contain a "T" at a particular position and 98 consensus sequences contain an "A" at the same position, then two consensus sequences have the sequence variation.

The term "the number of consensus sequences that do not have the sequence variation that comprise the position of a sequence variation" and grammatical equivalents thereof refer to the number of consensus sequences that do not contain the nucleotide sequence of a particular sequence variant. For example, if two consensus sequences contain a "T" at a particular position and 98 consensus sequences contain an "A" at the same position, then 98 consensus sequences do not have the sequence variation.

The term "total number of consensus sequences that comprise the position of a sequence variation" and grammatical equivalents thereof are intended to refer to the number of sequences that contain a nucleotide at a position that corresponds to the sequence variation, regardless of the identity of the nucleotide at that position. For example, if two consensus sequences contain a "T" at a particular position and 98 consensus contain an "A" at the same position, then total number of consensus sequences that comprise the position of the sequence variation is 100.

The terms "assessing the presence of" and "evaluating the presence of" include any form of measurement, including determining if an element is present and estimating the amount of the element. The terms "determining", "measuring", "evaluating", "assessing" and "assaying" are used interchangeably and include quantitative and qualitative determinations. Assessing may be relative or absolute. "Assessing the presence of" includes determining the amount of something present, and/or determining whether it is present or absent.

The term "microbial genome" refers to genetic material (DNA or RNA) that is microbial in origin (e.g., from a bacterium, virus or eukaryotic pathogen such as *Plasmodium, Leishmania*, or *Trypanosome*) that can be used as a template. A microbe may have, for example, a host-pathogen relationship with a mammal. In other cases, the microbial genome may be derived from the microbiome that is associated with the host. The term "microbial genome" is intended to include DNA genomes and RNA genomes (which can be readily reverse transcribed to DNA and then amplified by RT-PCR).

Other definitions of terms may appear throughout the specification. It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

DETAILED DESCRIPTION

Figure 2:
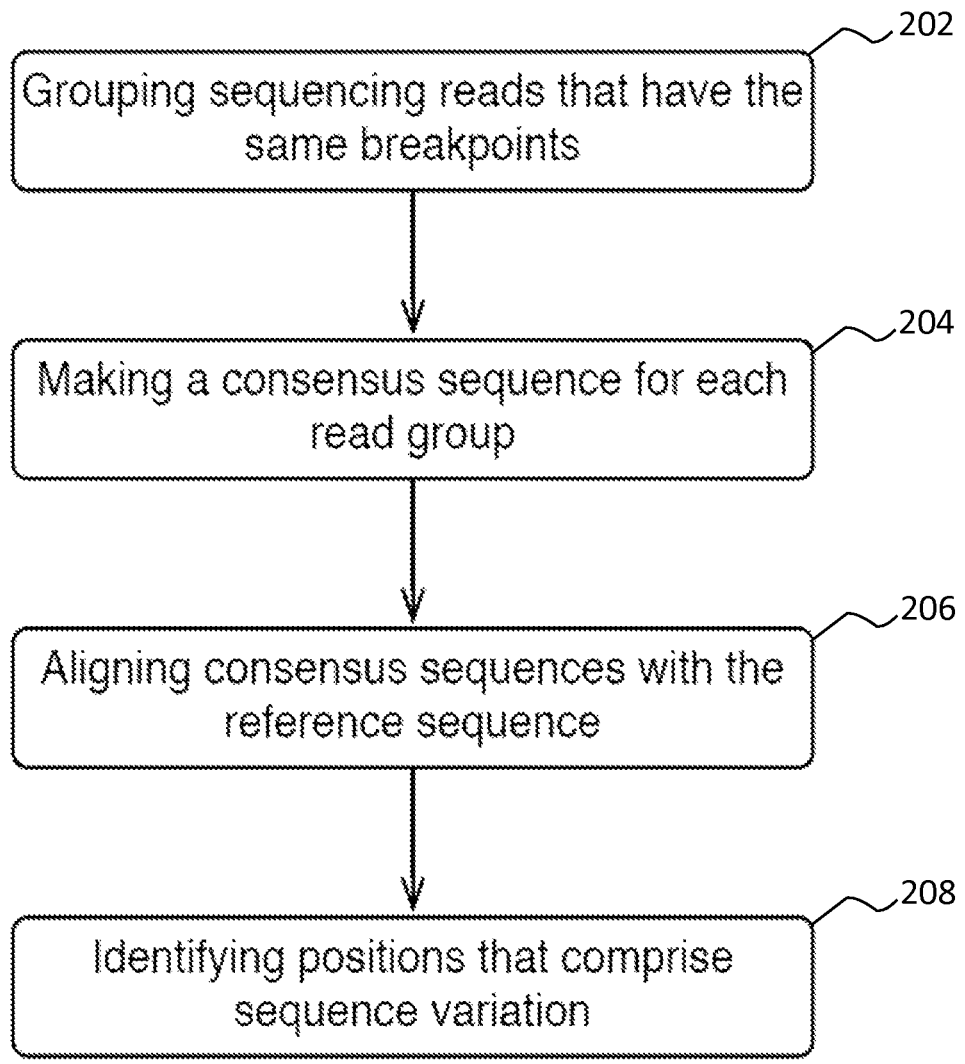
FIG. 2 is a flow-chart showing some of the data processing steps of one implementation of the present method.

Some of the principles of the method are shown in FIGS. 1 and 2. With reference to FIG. 1, the method is initiated by: a) amplifying a nucleic acid product from an initial sample (step 102 in FIG. 1). The product nucleic acid molecules produced in this step may be of any length, depending on how the method is implemented. In some embodiments, the product nucleic acid molecules may be 100 bp to 20 kb in length, although fragments that are at least 1 kb in length, e.g., 1 kb to 15 kb or 2 kb to 10 kb may be used in many cases. In some embodiments, the products may be over 50 kb in length if rolling circle or another isothermal amplification method is used. In certain embodiments, the initial amplification reaction may be multiplexed so that the initial amplification reaction results in multiple (e.g., 2, 3, 4, 5, or 6 or more) different amplicons, where each amplicon is a different target sequence in the template. The concentration of product made in this amplification step may be in the region of 0.05 ng/µl to 1 µg/µl, 0.5 ng/µl to 100 ng/µl. If necessary, the volume of product use in the next step can be adjusted in accordance with the concentration of the product. As would be apparent, this step of the method may be done by PCR or RT-PCR, although other methods may be used.

The nucleic acid (RNA or DNA) in the initial sample used in the method may be at any concentration and may be from any suitable source. In particular embodiments, the nucleic acid sample may comprise genomic DNA or RNA from a eukaryote, e.g., human, monkey, rat, fish, insect or plant, etc., particularly a mammal, or from a microbe, e.g., virus or a bacterium. The concentration of the template may vary greatly and need not be known before starting the method. In some embodiments, there may be 1, 2, 3, 4, 5, up to 10, up to 100, up to 500, up to 1,000, up to 5,000, up to 10,000, up to 50,000, up to 100,000, up to 1M, up to 10M, up to 100M or up to 1B initial template molecules or more in the sample. If this step is done by PCR or RT-PCR, then the PCR or RT-PCR may be done using 5-60 or cycles, e.g., 25-35 cycles.

Methods for extracting DNA and RNA from various samples, e.g., clinical, forensic, and environmental samples, are well known in the art. Samples include, but are not limited to, skin swab, skin biopsy, saliva, tooth swab, tooth scrapping, cheek swabs, throat swab, sputum, endogastric sample, feces, urine, vaginal, cervical, endocervical, endometrial, nasal swab, lung, organ biopsy, and tissue biopsy. A sample can also be a bodily fluid. Bodily fluids of interest include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit and urine. Methods for extracting DNA and RNA from such samples are well known.

In particular cases, the template may be microbial and, as such, may be or may contain, for example, the genome of a DNA virus, an RNA virus or a reverse transcribing virus, e.g., reovirus, rotavirus, enterovirus, rhinovirus, hepatovirus, cardiovirus, aphthovirus, poliovirus, parechovirus, erbovirus, kobuvirus, teschovirus, coxsackie, norwalk virus, rubella virus, alphavirus, lymphocytic choriomeningitis virus, dengue virus, hepatitis C virus, yellow fever virus, influenzavirus A, influenzavirus B, influenzavirus C, isavirus, thogotovirus, measles virus, mumps virus, respiratory syncytial virus, Rinderpest virus, canine distemper virus, California encephalitis virus, hantavirus, rabies virus, Ebola virus, Marburg virus, corona virus, astrovirus, borna disease virus, arterivirus, equine arteritis virus, hepatitis E virus, retroviruses (e.g., HIV-1 and HIV-2) and hepatitis B virus. Methods for amplifying viral sequences from such samples, e.g., by RT-PCR are well known.

The polymerase used in the initial amplification step may be any type of DNA polymerase. DNA polymerases can have 5' to 3' and/or 3' to 5' exonuclease activity. 'Proofreading' DNA polymerases are typically defined as those with 3' to 5' exonuclease activities. If this step is isothermal, then Bst 2.0, Bst LF, or phi29 DNA polymerase may be used. If the initial amplification is done by PCR, then a thermostable polymerase of bacterial or archael origin (or a variant thereof) may be used. Examples of non-proofreading thermostable polymerases (i.e., thermostable polymerases that don't have a 3' to 5' exonuclease activity) include, but are not limited to Taq and Tth. Examples of proofreading thermostable polymerases include, but are not limited to, Pfu (Agilent), Pwo (Roche), Tgo (Roche), VENT™ (NEB), DEEP VENT™ (NEB), KOD HiFi (Novagen), PFX50T™ (Life Technologies), HERCULASE III™ (Agilent), PLATINUM PFX™ (Life Technologies) and ProofStart (Qiagen). These polymerases, on average, produce 4× to 8× fewer errors than Taq polymerase. Further examples of proofreading thermostable polymerases include, but are not limited to, PHUSION™ (NEB), PFUULTRAT™ (Agilent), PFUULTRAT™ II (Agilent), IPROOFT™ (BioRad), and KAPAHIFIT™ (Kapa Biosystems). These polymerases, on average, produce at least 20× fewer errors than Taq polymerase and can readily amplify fragments of up to 15 kb.

Following the initial amplification step, a sequence variant may be present in the amplification product at a copy number of less than 1 in 10 (e.g., less than 1 in 20, less than 1 in 50, less than 1 in 100, less than 1 in 1,000, less than 1 in 10,000, less than 1 in 100,000, less than 1 in 1M or less than 1 in 10M) relative to other molecules that do not have the sequence variation. Different PCR products from the same sample may be pooled together after they have been amplified.

Next, the method comprises: b) fragmenting an amount of the nucleic acid product produced by step a) to produce fragments and c) attaching an adaptor to each end of the fragments created in step b) to produce adaptor-tagged fragments (step 104 in FIG. 1). These steps may be mediated by a transposase (see, e.g., Caruccio, Methods Mol. Biol. 2011; 733:241-55), in which case the steps may be done simultaneously, i.e., in the same reaction using a process that is often referred to as "tagmentation". In other embodiments, the fragmenting may be done mechanically (e.g., by sonication, nebulization, or shearing) or using a double stranded DNA "dsDNA" fragmentase enzyme (New England Biolabs, Ipswich Mass.). In some of these methods (e.g., the mechanical and fragmentase methods), after the DNA is fragmented, the ends are polished and A-tailed prior to ligation to the adaptor. In certain embodiments, the fragmenting may be done by a) amplifying a nucleic acid template using a dNTP mix that contains 5-methyl dCTP, thereby producing product nucleic acid molecules that contains methylcytosines; b) treating the product nucleic acid molecules with a methylation-dependent restriction enzyme, thereby cleaving the product nucleic acid molecules at sites that are adjacent to at least some of the methylcytosines and producing fragments of the product nucleic acid molecules; and c) ligating double-stranded adaptors that contain an overhangs that are compatible with the ends of the fragments to produce adaptor-ligated products. Such methods are described in UK patent application serial no. 1421003.3, filed on Nov. 26, 2014, which patent application is incorporated by reference herein. Depending on the fragmentation method used, this step may use a defined amount of nucleic acid product, e.g., 0.1 ng to 1 µg of product. In several cases though, this step may simply use a volume of the amplified product, without measuring the concentration of the product.

The average size of the fragments produced in this step of method may be shorter than the length of a single sequence read or paired end read on the sequence platform used. In some cases, the average size of the fragments may be in the range of 100-1,000 bp, e.g., 150-700 nucleotides in length, although it is expected that longer fragments may be used as sequence reads become longer as technology develops.

The adaptors provide binding sites for PCR primers that are used in the next amplification step of the method and, as such, they usually are at least 12 bp long (e.g., at least 15 bp or at least 20 bp long). In certain cases, a Y adaptor, e.g., adaptor that contains: a double-stranded region and a single-stranded region in which the oligonucleotides are not complementary, may be used. In these cases, the end of the double-stranded region ligates to the fragments, and each strand of the product is asymmetrically tagged in that it has the sequence of one strand of the Y-adaptor at one end and the other strand of the Y-adaptor at the other end. In other embodiments, a loop adaptor (as described in U.S. Pat. No. 8,420,319) may be used.

In certain cases the adaptor may additionally contain a molecule identifier sequence that assists in distinguishing the ligated molecules from one another after they have been amplified. In certain cases, the molecule identifier sequence may be error-correcting, meaning that even if there is an error (e.g., if the sequence of the molecular barcode is mis-synthesized, mis-read or is distorted by virtue of the various processing steps leading up to the determination of the molecular barcode sequence) then the code can still be interpreted correctly. Descriptions of exemplary error correcting sequences can be found throughout the literature (e.g., US20100323348 and US20090105959, which are both incorporated herein by reference). Such a molecule identifier sequence, and any other additional sequences, e.g., RNA polymerase promoters, sample identifiers, etc., should be positioned between the end that is ligated to the fragments and the primer binding sites. If a molecule identifier sequence is used, it can be of relatively low complexity (e.g., may be composed of a mixture of 8 to 1024 different sequences). Alternatively, in some embodiments the molecule identifier sequence may be of high complexity, depending on the number of unique fragments that require identification.

A molecule identifier sequence (if one is desired) can also be added to the adaptor-ligated fragments by primer extension, as described in, e.g., U.S. Pat. No. 8,728,766 and as illustrated by example in FIG. 6. In these embodiments, a primer that contains a 5' tail that contains the molecule identifier sequence and a 3' end that hybridizes to the adaptor added to the fragments is extended using the fragments as a template, thereby producing a copy of the fragments. Using this method, the copied fragments will contain the molecular barcode at the 5' end.

Next, the method comprises: d) sampling no more than 10% of the product of step c) (step 106 in FIG. 1) and amplifying the adaptor-tagged fragments contained in the sampled product using one or more primers that hybridize to the adaptor to produce copies of the fragments (step 108 in FIG. 1). As noted above, the term "sampling" is intended to mean that a relatively minor portion of the adaptor-tagged sample is used in the second amplification reaction. Depending on how much of the adaptor-tagged sample is used, the sampling may involve diluting part of the adaptor-tagged sample into a larger volume and then removing a portion of the diluted sample (e.g., in the range of 0.5 µl to 10 µl) for use in the next step of the method. In certain cases, the sampling step may involve sampling no more than 10%, no more than 5%, no more than 1%, no more than 0.5%, no more than 0.1%, no more than 0.05%, no more than 0.01%, no more than 0.005%, no more than 0.001%, no more than 0.0005%, no more than 0.0001%, no more than 0.00005%, or no more than 0.00001%, of the product of step c). In some cases, the portion of the tagged nucleic acid sample used in step d) may be less than 1/100th (e.g., less than 1/500th, 1/5,000$^{th}$, 1/50,000$^{th}$, 1/500,000th or 1/5,000,000th) of the product of step c). The rest of the adaptor-tagged sample (which may represent at least 99% of the volume of the sample, may be discarded or stored for future use). Depending on how much of the tagged sample is sampled, this amplifying step may result in amplification of less than 1 in 1,000 (e.g., less than 1 in 5,000, less than 1 in 10,000, less than 1 in 50,000, less than 1 in 100,000, less than 1 in 500,000 or less than 1 in 1,000,000) of the fragments produced in step b). As would be apparent, because the primers used hybridize to sequences that are in the added adaptors, this step amplifies the tagged molecules (although there may be some bias for shorter fragments, or regions of high or low GC content, as is common in some protocols).

Amplification step 108 may also be done using a variety of polymerases, including proof-reading polymerases, many of which are described above. In some embodiments, a limited number of PCR cycles, e.g., 5 to 40, 5 to 15 or 5 to 10, may be used. In some embodiments, this step may be done using a single primer, e.g., using SPIA (Single Primer Isothermal Amplification), although several other amplification methods could be used.

The amount of the adaptor-tagged fragments that are sampled (e.g., whether a 100th, a 1,000th or a 10,000th, etc., of the adaptor-tagged sample is used in the next step) can vary depending upon the desired number of sequence reads for each amplified fragment (where a sequence read corresponds to a copy of the fragment). If more sequence reads per fragment are desired, then less adaptor-tagged sample may be used and if fewer sequence reads per fragment are desired, then more adaptor-tagged sample should be sampled. The amount of the adaptor-tagged fragments sampled in step 106 may be selected to provide at least two, e.g., at least 2, at least 3, at least 5, at least 10, or at least 20, consensus sequences for a potential sequence variant. The sampling step ensures that multiple reads with the same start- and end-end points are obtained, thereby allowing those sequences to be grouped.

As would be apparent, the adaptor-tagged fragments may be amplified using primers that hybridize to the adaptors, thereby producing amplification products. In some cases, the primers used to amplify the fragments may have a 5' tail that provides compatibility with a particular sequencing platform. In certain embodiments, one or more of the primers used in this step may additionally contain a sample identifier. If the primers have a sample identifier, then products from different samples can be pooled prior to sequencing. In some embodiments, this amplifying step (step d) may comprise appending sample identifier sequence to the amplified fragments.

The primers used for amplification step 108 may be compatible with use in any next generation sequencing platform in which primer extension is used, e.g., Illumina's reversible terminator method, Roche's pyrosequencing method (454), Life Technologies' sequencing by ligation (the SOLiD platform), Life Technologies' Ion Torrent platform or Pacific Biosciences' fluorescent base-cleavage method. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513:19-39) English (PLoS One. 2012 7: e47768) and Morozova (Genomics. 2008 92:255-64), which are incorporated by reference for the general descriptions of the methods and the particular steps of the methods, including all starting products, reagents, and final products for each of the steps.

Next, the method comprises e) sequencing at least some of the copies of the fragments produced in d) to produce a plurality of sequence reads (step 110 in FIG. 1). This step may be done using any convenient next generation sequencing method and may result in at least 10,000, at least 50,000, at least 100,000, at least 500,000, at least 1M at least 10M at least 100M or at least 1B sequence reads. In some cases, the reads are paired-end reads.

Figure 7:
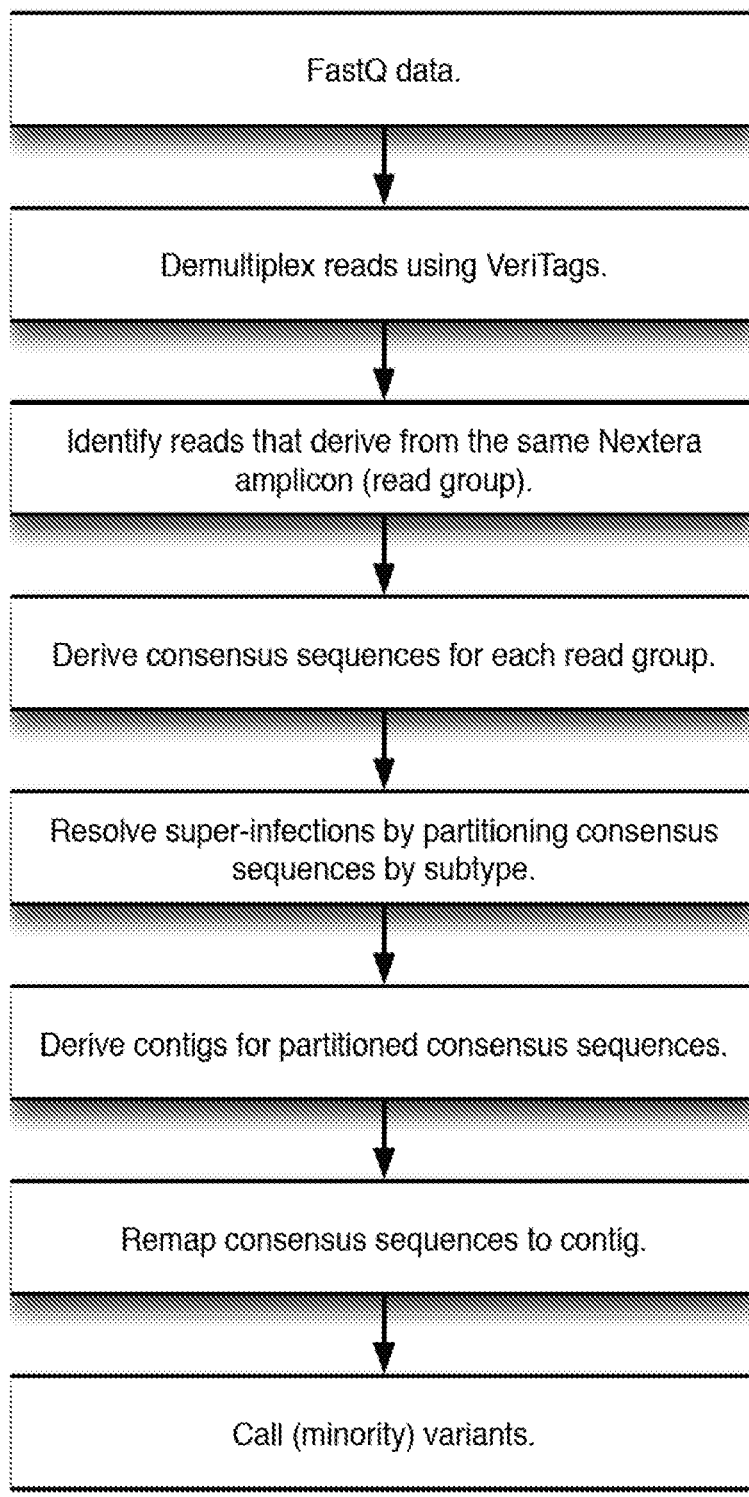
FIG. 7 shows an exemplary data processing workflow for the present method.

The computational steps described may be computer-implemented steps and, as such, instructions for performing the steps may be set forth as programming that may be recorded in a suitable physical computer readable storage medium. Sequencing reads are analyzed computationally (step 112 in FIG. 1). The general principles of some of the analysis steps are shown in FIG. 2 and FIG. 7.

In some implementations, initial processing of sequencing data includes identification of molecular barcodes (including sample identifiers or molecule identifier sequences), and trimming reads to remove low quality or adaptor sequences. In addition, quality assessment metrics can be run to ensure that the dataset is of an acceptable quality.

Sequence reads of copies of fragments that have the same fragmentation breakpoints and that are substantially identical sequences are then grouped into "read groups" (step 202 in FIG. 2). Fragments with the same fragmentation breakpoints have substantially identical sequences at positions adjacent to the adaptor. These can be identified in paired-end reads as substantially identical 5' sequences from both read 1 and read 2. Similarly, single-end reads that traverse both breakpoints can be used to identify sequences adjacent to both adaptor sequences. In some embodiments fragments with the same fragmentation breakpoints can be identified using one, or other, of the sequences at one, or other, of the sequences adjacent to the adaptor. In some embodiments, reads are trimmed to remove adaptor sequences, overhang sequences for ligation and the like. For example, all of the sequence reads in a read group may have a contiguous sequence of at least 10, 15, 20 or 30 nucleotides at the 5' end that are substantially identical to one another and a contiguous sequence of at least 10, 15, 20 or 30 nucleotides at the 3' end that are substantially identical to one another. The identification of copies of fragments that have the same fragmentation breakpoints can be done using: (1) start, end coordinates alone, (2) molecule identifier sequences alone or (3) both start, end coordinates and identifier sequences. The method is best implemented by method (3). The use of both molecule identifier sequences and the start-end points to define fragments comprising a read group adds significant robustness to the grouping step because: (1) There is more latitude in the dilution. If there are "too many" fragments (i.e. insufficient dilution), the molecule identifier sequences would help identify individual molecules that have, by chance, the same start-end point. (2) Molecule identifier sequences aid identification of individual molecules even if fragmentation is biased. (3) Using a combination of start and end points and molecule identifier sequences reduces the number of molecule identifier sequences that need to be synthesized, which is useful if error-correctable identifier sequences (which are individually synthesized) are used rather than degenerate tags (which are usually synthesized as a pool).

In embodiments that use molecule identifier sequences, those sequences are added to the fragments prior to amplification, either by ligation, primer extension (primer extension may be done as the first step of the amplification reaction; see, e.g., FIG. 6) or using a transposase enzyme. In these embodiments, the grouping step may done by identifying which sequence reads have the have substantially the same start and end sequences and molecule identifier sequence. In these embodiments, the molecule identifier sequence may be error correctable and it may be of relatively low complexity (e.g., may be composed of a mixture of 8 to 1024 different sequences), although higher complexity molecule identifier sequences can be used in some cases.

After the sequences have been grouped by their fragmentation breakpoints and/or molecule identifiers, the method comprises g) deriving a consensus sequence for each of the read groups (step 204 in FIG. 2). In this step, a single sequence that represents the most likely base at each position in the reads is determined for each of the read groups. In some embodiments, the most likely base is derived by counting the number of reads in the read group with a given base call at a given position. In other embodiments, the most likely base is derived using base quality scores, or recalibrated base quality scores (see: A framework for variation discovery and genotyping using next generation DNA sequencing data. DePristo M, Banks E, Poplin R, Garimella K, Maguire J, Hartl C, Philippakis A, del Angel G, Rivas M A, Hanna M, McKenna A, Fennell T, Kernytsky A, Sivachenko A, Cibulskis K, Gabriel S, Altshuler D, Daly M, 2011 NATURE GENETICS 43:491-498), and other metrics that are obtained in performing the method. In further embodiments, the most likely base is derived using a combination of base call counts, base qualities and other data. This step is illustrated by example in FIG. 3. As noted above, the number of reads per group may vary greatly and, in certain cases, may be in the range of 2-100 or more. The generation of consensus sequences reduces the effects of errors in sequencing (e.g., base mis-calls) and errors caused by a polymerase (whether used in amplification or sequencing steps) mis-incorporating a base and, as such, consensus sequences that are derived from more sequence reads more accurately reflect the actual sequence of the initial template (rather than, e.g., a sequencing or PCR error).

In some embodiments, the total number of reads in the read group, the number of bases that match the consensus base call, quality scores and other data can be used to provide a quality metric for each base in the consensus sequence and/or an overall metric that describes the quality of the consensus sequences. In one embodiment, base calls at a specific position that disagree with the consensus base call are considered to be errors due to errors in the library preparation or sequencing. These positions can be aggregated using base quality or count data. Which positions within a read group were corrected are recorded as well as how difficult it was to choose a base for that position in the read group, and which bases were included as possibilities. This information can be further used in subsequent variant calling steps.

After the consensus sequences have been produced, the method comprises aligning the consensus sequences with a reference sequence (step 206 in FIG. 2); and identifying the positions in the alignment that comprise sequence variation (step 208 in FIG. 2). In this step, the reference sequence may be from any suitable source. For example, the reference sequence may be a public sequence (e.g., from NCBI's GenBank database), a sequence that is not public (e.g., from an in-house sequencing effort) or a sequence that has been assembled de novo from the sequence reads generated in course of performing the method.

Any alignment algorithm, including Smith Waterman, Needleman Wunsch, BLAST and others, may be used for alignment of a query to reference sequence. In some cases, an optimal alignment may require adjustment of some of the parameters used, such as, for Smith Waterman or Needleman Wunsch, affine parameters, including match score, mismatch penalty, gap opening penalty, and gap extension penalty. Some alignment algorithms use additional data from paired-end reads or base quality scores. The results of alignment algorithms are typically recorded in SAM or BAM format (see, e.g., Bioinformatics. Aug. 15, 2009; 25(16): 2078-2079), although no limitation is intended in this regard. In some cases, a process known as indel realignment is used to refine the alignment. Indel realignment algorithms assess evidence for an insertion/deletion in the alignment data and adjust the alignment accordingly (see DePristo, supra).

In an alternative embodiment, the order of steps in the workflow can be altered; for example, reads can be aligned to a reference sequence based on mapping coordinates of one read or both reads if paired-end reads before read groups are identified. The mapping step could occur before or after assignment of a read to a sample identifier. No limitation is intended in this regard.

With consensus sequences aligned to a reference, one can begin to identify variants at either the single nucleotide or codon level. However, when a base call is observed in a minority of alignments, it is difficult to determine whether the variant is a true positive i.e. a biological difference, or a false positive i.e. an error that has occurred in the workflow. Several sources of information can be used to determine whether a sequence variant is a true positive or false positive, and/or to estimate the abundance of the sequence variation in the sample. For example, these include: (1) the number of consensus sequences with a variant call compared to the total number of consensus sequences at a given position in the alignment; (2) the overall quality assessment of the consensus sequence(s) in which a sequence variant is found compared to other consensus sequences in which the variant is not found; (3) the specific quality assessment of the consensus sequence base in which a sequence variant is identified compared to consensus sequences in which the variant is not found; (4) the number of reads that make up read groups used to derive each consensus sequence; (5) whether a variant is present in consensus sequences that map in both orientations to the reference (strand bias); (6) the type of mutation (e.g. premature stop codon versus substitution) and (7) prior knowledge of variant positions.

In certain cases, in addition to the above information, a determination of whether a sequence is a true positive or false positive may also incorporate an error model that estimates the likelihood that a given sequencing and/or PCR error might occur. Several source of information can be used in this assessment: (1) a base transition probability matrix (Statistical Methods in Bioinformatics: An Introduction by Warren J. Ewens, Gregory R. Gran). In one embodiment, the matrix can be estimated during consensus sequence derivation. For example, the number of reads at a given position in a read group that either agree or disagree with the most likely consensus base can be used to estimate transition probabilities. (2) The sequence context of a variant, e.g. whether the variant is adjacent to a homopolymer run. (3) Known sequencer error modalities, such as sequencing cycle number. (4) Performance characteristics of sequencing positive and/or negative controls.

In general, if no or very little error correction was required to establish the consensus sequence of the read groups exhibiting a variant base, and that base was rarely called in place of the reference, one can be confident that the base is a true variant reflected in the biological sample. However, if a medium to high level of error correction was required to establish the consensus sequence for the read groups exhibiting the variant and the variant is a more commonly recorded mutation, one can be less confident that the base is a true variant. Because the confidence has been recorded throughout the informatic pipeline, one is able to provide a report of the number and type of variant bases in each sample, as well as an assessment of how confident one is that the reporting is correct. In some exemplary embodiments, the identified variants may be compared to the known mutations of clinical significance in order to produce a clinical report of a patient's drug resistance.

In certain embodiments, the method may comprise:

a) amplifying a nucleic acid product from an initial template;

b) fragmenting a defined amount of the nucleic acid product produced by step a) to produce fragments;

c) attaching an adaptor to each end of the fragments created in step (b)

d) amplifying less than 1 in 100 of the fragments produced in step c), using one or more primers that hybridize to an attached adaptor, to produce copies of the fragments;

e) sequencing at least some of the copies of the fragments produced in d) to produce a plurality of sequence reads;

f) computationally grouping sequence reads for copies of fragments that have the same fragmentation breakpoints and substantially identical sequences;

g) deriving a consensus sequence for computationally grouped sequencing reads;

h) counting the number of consensus sequences for the sequence variant; and i) making a determination of whether the sequence variant is in the sample, wherein a higher number of consensus sequences for the sequence variant increase the confidence of the determination.

In certain cases, the number of copies of a particular variant in the initial population of template molecules is unknown. In some embodiments, the concentration of template molecules in the initial population of template molecules is unknown, i.e., the method may comprise amplifying a nucleic acid product from an initial template population of unknown copy number.

The final evaluating step may be focused on nucleotides that are known to vary in the template under study, e.g., positions that correspond to mutations are known to cause resistance in in HIV-1 and other microbial genomes (see, e.g., Top Antivir Med. 2014 22:642-650). Alternatively, the method can be used to systematically analyze all of the positions, thereby identifying and/or quantifying all potential variants in the sample.

The method described finds use in a variety of applications, where such applications generally include sample analysis applications in which the presence of a minority variant in a nucleic acid sample needs to be detected or measured.

As noted above, the method may be used, among other things, as a prognostic or to make a treatment decision for a patient that is infected with an infectious agent, e.g., a virus or bacteria, where the minority variant may cause drug resistance.

The following table provides an exemplary list of codons at which mutations cause drug resistance in HIV-1. In certain cases, the final step of the present method may be used to identify and/or quantify minority variants that have mutations in at least some of these positions.

| Protein | Drug Resistance | Codons |
| --- | --- | --- |
| Reverse transcriptase | Multi | 41, 62, 69, 70, 210, 215, 219 |
| Reverse transcriptase | Multi | 62, 75, 77, 116, 151, |
| Reverse transcriptase | Multi | 41, 67, 70, 210, 215, 219 |
| Reverse transcriptase | Abacavir | 65, 74, 115, 184 |

-continued

| Protein | Drug Resistance | Codons |
|---|---|---|
| Reverse transcriptase | Didanosine | 65, 74 |
| Reverse transcriptase | Emtricitabine | 65, 184 |
| Reverse transcriptase | Lamivudine | 65, 184 |
| Reverse transcriptase | Stavudine | 41, 65, 67, 70, 210, 215, 219 |
| Reverse transcriptase | Tenofovir | 65, 70 |
| Reverse transcriptase | Zidovudine | 41, 67, 70, 210, 215, 219 |
| Reverse transcriptase | Efavirenz | 100, 101, 103, 106, 108, 181, 188, 190, 225, 230 |
| Reverse transcriptase | Etravirine | 90, 98, 100, 101, 106, 138, 179, 181, 190, 230 |
| Reverse transcriptase | Nevirapine | 100, 101, 103, 106, 108, 181, 188, 190, 230 |
| Reverse transcriptase | Rilpivirine | 100, 101, 138, 179, 181, 188, 221, 227, 230 |
| Protease | Atazanavir +/− ritonavir | 10, 16, 20, 24, 32, 33, 34, 36, 46, 48, 50, 53, 54, 60, 62, 64, 71, 73, 82, 84, 85, 88, 90, 93 |
| Protease | Darunavir +/− ritonavir | 11, 32, 33, 47, 50, 54, 74, 76, 84, 89 |
| Protease | Fosamprenavir +/− ritonavir | 10, 32, 46, 47, 50, 54, 73, 76, 82, 84, 90 |
| Protease | Indinavir +/− ritonavir | 10, 20, 24, 32, 36, 46, 54, 71, 73, 76, 77, 82, 84, 90 |
| Protease | Lopinavir +/− ritonavir | 10, 20, 24, 32, 33, 46, 47, 50, 53, 54, 63, 71, 73, 76, 82, 84, 90 |
| Protease | Nelfinavir | 10, 30, 36, 46, 71, 77, 82, 84, 88, 90 |
| Protease | Saquiavir +/− ritonavir | 10, 24, 48, 54, 62, 71, 73, 77, 82, 84, 90 |
| Protease | Tipranavir +/− ritonavir | 10, 33, 36, 43, 46, 47, 54, 58, 69, 74, 82, 83, 84, 89 |
| Envelope | Enfuvirtide | 36, 37, 38, 39, 40, 42, 43 |
| Integrase | Doluteravir | 121, 138, 140, 148 |
| Integrase | Elvitegavir | 66, 92, 97, 121, 147, 148, 155 |
| Integrase | Raltegravir | 74, 92, 97, 121, 138, 140, 143, 148, 155 |

The following table provides an exemplary list of codons at which mutations cause drug resistance in HCV. In certain cases, the final step of the present method may be used to identify and/or quantify minority variants that have mutations in at least some of these positions.

| Protein | Drug Resistance | Codons |
|---|---|---|
| NS3 protease | boceprevir | 36, 54, 55, 155, 156, 158, 168, 170, 175 |
| NS3 protease | telaprevir | 36, 54, 132, 155, 156, 168 |
| NS3 protease | simeprevir | 80, 122, 155, 168, 179 |
| NS3 protease | vaniprevir | 43, 155, 168 |
| NS3 protease | BI-201335 | 155, 156, 168 |
| NS5A Domain I | daclatasvir | 28, 30, 31 and 93 |
| NS5B Polymerase | sofosbuvir | 282 |

In other embodiments, the above-described methods may be employed to diagnose, to predict a response to treatment, or to investigate a cancerous condition or another mammalian disease, including but not limited to, leukemia, breast carcinoma, prostate cancer, Alzheimer's disease, Parkinsons's disease, epilepsy, amylotrophic lateral schlerosis, multiple sclerosis, stroke, autism, mental retardation, and developmental disorders. Additionally, the above-described methods may be employed to diagnose, to predict a response to treatment, or to investigate a disease that is caused by mitochondrial heteroplasmy. Many nucleotide polymorphisms are associated with, and are thought to be a factor in, producing these disorders. Knowing the type and the location of the nucleotide polymorphism may greatly aid the diagnosis, prognosis, and understanding of various mammalian diseases. In addition, the assay conditions described herein can be employed in other nucleic acid detection applications including, for example, for the detection of infectious diseases, viral load monitoring, viral genotyping, environmental testing, food testing, forensics, epidemiology, and other areas where specific nucleic acid sequence detection is of use. In certain embodiments, the method may be used to analyze cell-free DNA obtained from a pregnant female, for example to identify circulating tumor DNA or RNA.

In some embodiments, a biological sample may be obtained from a patient, and the sample may be analyzed using the method. In particular embodiments, the method may be employed to identify and/or estimate the amount of mutant copies of a genomic locus that are in a biological sample that contains both wild type copies of a genomic locus and mutant copies of the genomic locus, where the mutant copies have a sequence variation relative to the wild type copies of the genomic locus. In this example, the sample may contain at least 100 times (e.g., at least 1,000 times, at least 5,000 times, at least 10,000 times, at least 50,000 times, at least 100,000 times, at least 1 M times or at least 10M times) more wild type copies of the genomic locus than mutant copies of the genomic locus.

In these embodiments, the method may be employed to detect an oncogenic mutation (which may be a somatic mutation) in, e.g., PIK3CA, NRAS, KRAS, JAK2, HRAS, FGFR3, FGFR1, EGFR, CDK4, BRAF, RET, PGDFRA, KIT or ERBB2, which may be associated with breast cancer, melanoma, renal cancer, endometrial cancer, ovarian cancer, pancreatic cancer, leukemia, colorectal cancer, prostate cancer, mesothelioma, glioma, medulloblastoma, polycythemia, lymphoma, sarcoma or multiple myeloma (see, e.g., Chial 2008 Proto-oncogenes to oncogenes to cancer. Nature Education 1:1).

In some embodiments, a sample may be collected from a patient at a first location, e.g., in a clinical setting such as in a hospital or at a doctor's office, and the sample may be forwarded to a second location, e.g., a laboratory where it is processed and the above-described method is performed to generate a report. A "report" as described herein, is an electronic or tangible document which includes report elements that provide test results that may indicate the presence and/or quantity of minority variant(s) in the sample. Once generated, the report may be forwarded to another location (which may the same location as the first location), where it may be interpreted by a health professional (e.g., a clinician, a laboratory technician, or a physician such as an oncologist, surgeon, pathologist or virologist), as part of a clinical decision.

The informatics steps of the above-described method can be implemented on a computer. In certain embodiments, a general-purpose computer can be configured to a functional arrangement for the methods and programs disclosed herein. The hardware architecture of such a computer is well known by a person skilled in the art, and can comprise hardware components including one or more processors (CPU), a random-access memory (RAM), a read-only memory (ROM), an internal or external data storage medium (e.g., hard disk drive). A computer system can also comprise one or more graphic boards for processing and outputting graphical information to display means. The above components can be suitably interconnected via a bus inside the computer. The computer can further comprise suitable interfaces for communicating with general-purpose external components such as a monitor, keyboard, mouse, network, etc. In some embodiments, the computer can be capable of parallel processing or can be part of a network configured for parallel or distributive computing to increase the processing power for the present methods and programs. In some embodiments, the program code read out from the storage medium can be written into memory provided in an expanded board inserted in the computer, or an expanded unit connected to the computer, and a CPU or the like provided in the expanded board or expanded unit can actually perform a part or all of the operations according to the instructions of the program code, so as to accomplish the functions described below. In other embodiments, the method can be performed using a cloud computing system. In these embodiments, the data files and the programming can be exported to a cloud computer that runs the program and returns an output to the user.

A system can, in certain embodiments, comprise a computer that includes: a) a central processing unit; b) a main non-volatile storage drive, which can include one or more hard drives, for storing software and data, where the storage drive is controlled by disk controller; c) a system memory, e.g., high speed random-access memory (RAM), for storing system control programs, data, and application programs, including programs and data loaded from non-volatile storage drive; system memory can also include read-only memory (ROM); d) a user interface, including one or more input or output devices, such as a mouse, a keypad, and a display; e) an optional network interface card for connecting to any wired or wireless communication network, e.g., a printer; and f) an internal bus for interconnecting the aforementioned elements of the system.

The memory of a computer system can be any device that can store information for retrieval by a processor, and can include magnetic or optical devices, or solid state memory devices (such as volatile or non-volatile RAM). A memory or memory unit can have more than one physical memory device of the same or different types (for example, a memory can have multiple memory devices such as multiple drives, cards, or multiple solid state memory devices or some combination of the same). With respect to computer readable media, "permanent memory" refers to memory that is permanent. Permanent memory is not erased by termination of the electrical supply to a computer or processor. Computer hard-drive ROM (i.e., ROM not used as virtual memory), CD-ROM, floppy disk and DVD are all examples of permanent memory. Random Access Memory (RAM) is an example of non-permanent (i.e., volatile) memory. A file in permanent memory can be editable and re-writable.

Operation of the computer is controlled primarily by an operating system, which is executed by the central processing unit. The operating system can be stored in a system memory. In some embodiments, the operating system includes a file system. In addition to an operating system, one possible implementation of the system memory includes a variety of programming files and data files for implementing the method described below. In certain cases, the programming can contain a program, where the program can be composed of various modules, and a user interface module that permits a user to manually select or change the inputs to or the parameters used by the program. The data files can include various inputs for the program.

In certain embodiments, instructions in accordance with the method described herein can be coded onto a computer-readable medium in the form of "programming," where the term "computer readable medium" as used herein refers to any storage or transmission medium that participates in providing instructions and/or data to a computer for execution and/or processing. Examples of storage media include a floppy disk, hard disk, optical disk, magneto-optical disk, CD-ROM, CD-R, magnetic tape, non-volatile memory card, ROM, DVD-ROM, Blue-ray disk, solid state disk, and network attached storage (NAS), whether or not such devices are internal or external to the computer. A file containing information can be "stored" on computer readable medium, where "storing" means recording information such that it is accessible and retrievable at a later date by a computer.

The computer-implemented method described herein can be executed using programs that can be written in one or more of any number of computer programming languages. Such languages include, for example, Java (Sun Microsystems, Inc., Santa Clara, Calif.), Visual Basic (Microsoft Corp., Redmond, Wash.), and C++ (AT&T Corp., Bedminster, N.J.), as well as any many others.

In any embodiment, data can be forwarded to a "remote location," where "remote location," means a location other than the location at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

Some embodiments include implementation on a single computer, or across a network of computers, or across networks of networks of computers, for example, across a network cloud, across a local area network, on hand-held computer devices, etc. In certain embodiments, one or more of the steps described herein are implemented on a computer program(s). Such computer programs execute one or more of the steps described herein. In some embodiments, implementations of the subject method include various data structures, categories, and modifiers described herein, encoded on computer-readable medium(s) and transmissible over communications network(s).

Software, web, internet, cloud, or other storage and computer network implementations of the present invention could be accomplished with standard programming techniques to conduct the various assigning, calculating, identifying, scoring, accessing, generating or discarding steps.

The following patent publications are incorporated by reference for all purposes, particularly for methods by which nucleic acid molecules may be manipulated, reagents for doing the same, for sequencing library preparation workflow, sequencing methods, data processing methods, and for definitions of certain terms: U.S. Pat. No. 8,481,292, WO2013128281, WO2013000824 and Casbon Nuc. Acids Res. 2011, 22 e81, US20120122737, U.S. Pat. No. 8,476, 018 and all references cited above and below.

In certain implementations of the present method, molecule identifier sequences are used to increase the confidence of minority variant detection in sequence-based diagnostics. This method addresses issues of PCR error and recombination, differential amplification and sequencing errors. Briefly, individual fragments are tagged, by primer extension or ligation, with a molecule identifier sequence. After tagging, the association between the molecule identifier sequence and a fragment is maintained during subsequent manipulations including PCR and sequencing. The molecule identifier sequence assists in computationally organizing sequence reads into read groups, where each group derives from a single starting fragment. A consensus sequence is derived from the reads in each group. The consensus substantially reduces errors from late PCR cycles and NGS because false-positive variants are associated with only a fraction of the overall reads originating from the same template molecule.

Molecule identifier sequences are described in (Casbon Nuc. Acids Res. 2011, 22 e81) and have been demonstrated to increase the sensitivity of minority variant detection in HIV (Jabara et al 2011), Pap smears (Kinde et al 2013) and RNA-Seq (Shiroguchi et al 2012). To test the performance of the workflow described herein, a comparison was performed in a synthetic mixing experiment with minority variants at a level of 0.1% and ultra-high-deep sequencing depth of 50,000×; minority variant calls were made using read or molecule identifier sequences frequency as described below. False-positive base calls were removed from the reads using error correction, as employed by sequence assemblers (Pevzner et al 2001, Li et al 2010, Simpson et al 2012). The error correction algorithms split reads into overlapping kmers, and assume that kmers covering a false-positive base occur in a low number of reads in the entire dataset. kmer error correction based on read frequency was compared to kmer error correction based on molecule identifier sequence (VeriTag) frequency. Error-correction based on read frequency alone achieved 100% sensitivity but only 51.2% specificity (read thresholds were set to achieve maximum specificity whilst detecting all minority variant kmers). In contrast, for the same dataset, error correction based on molecule identifier sequence frequency achieved 100% sensitivity and 100% specificity. Taken together, these data suggest that error correction using molecule identifier sequence data provides robust and high confidence minority variant detection. As described below, this approach can be combined with other processes to address properly those issues that are encountered in minority detection in viral or microbiological genomes.

HIV-1 and HCV are examples that present specific challenges for analysis due to the high diversity of viral sequences and the wide range of viral titers. The main (M) group of HIV-1 includes nine major subtypes (A-D, F-H, J and K), four sub-subtypes (A1 and A2, F1 and F2) and over 55 circulating recombinant forms. HCV has eleven genotypes (1-11), each comprised of multiple subtypes (for example, 1a and 1b). The level of diversity makes it difficult to design primers capable of reliably amplifying viruses across different genotypes and subtypes.

This primer design constraint argues for long-amplicons instead of short, tiled amplicons as others have used; with longer amplicons fewer primers are required and thus there is greater flexibility with respect to the genomic positions of the primers. Unfortunately, in some instances, molecule identifier sequences per se (as previously described in Casbon and also as implemented by other groups using similar approaches) cannot be adapted easily to longer amplicons used in the workflow described in this patent application because the sequence reads do not cover the entire amplicon. An additional important consideration for the workflow proposed herein is the wide dynamic range is required to quantitate both low viral loads in patients responding to anti-retroviral therapy (ART) and high viral loads in infected individuals who are yet to start treatment. HIV quantitative RT-PCR assays are designed for widely varying viral loads of between 40 and $10^7$ copies/mL (Abbott, Roche). Similarly, HCV quantitative RT-PCR assays are designed for viral loads between 12 and $10^8$ IU/mL (Abbott) (IUs are international units, a calibrated WHO HCV RNA standard). Use of molecule identifier sequences relies on efficient distribution of raw sequencing reads across all the read groups. A major determinant of the number of reads in each read group is the number of input molecules into the molecule identifier sequence tagging reaction. Too many input molecules result in read groups with too few reads to generate a consensus sequence. In contrast, too few input molecules results in read groups with more reads than is necessary to generate a consensus sequence.

These conflicting concerns have inherent tradeoffs: for example, one might want to sequence a given population of molecules and identify variant molecules present at low frequency, e.g., 1 in every 100 molecules, but one is limited by the number of reads that one can generate on a sequencer.

First, one should ensure that one sequences enough different molecules. If, for example, only 10 different molecules were sequenced then one might, or might not, detect a variation that is present in 1 in every 100 molecules. If, however, one sequenced 500 different molecules, then one would have higher confidence that one would observe the variant molecule. This suggests that one should try to sequence as many different molecules as possible in order to maximize the chances of sequencing variant molecules.

The above approach should also take into account sequencing errors. If, for example, a variant is present in 1 in 100 molecules and one performs a sequencing experiment in which every read comes from a different molecule, then one would expect the variant to occur in approximately 1 in every 100 reads. However, if the sequencing error rate approaches 1 in 100 and errors are random, independent or identically distributed, then one would have difficulty in distinguishing a sequencing error from a bona fide variant. This problem can be overcome by sequencing copies of one molecule multiple times and building a consensus sequence. That way, one can identify, and correct, sequencing errors. For a defined sequencing capacity of a next generation sequencing system, one should try to limit the number of different molecules that are sequenced in order to sequence more copies of each molecule and build up a more accurate consensus sequences.

Two considerations compete: on the one hand, one may want to sample as many different molecules as possible in order to maximize the chances of sequencing a minor variant molecule. On the other hand, one may want to sequence copies of the same molecule as many times as possible in order to build an increasingly accurate consensus. Also, sequence reads can be "wasted" by sequencing copies of one molecule too many times. For example, one might gain sufficient confidence from, e.g., 10 reads, and therefore sequencing copies of one molecule 100 times would be unnecessary.

The solution to this conundrum is to introduce a sampling step in which only a given relatively small portion of the sample is used in the next step. This sampling step is a key element of the workflow herein and serves multiple purposes. First, it controls the total number of molecules that can be sequenced. Second, because it is followed by amplification of the sampled molecules, it controls and defines the probability of sequencing the copies of the same molecule multiple times so one can generate a consensus and eliminate sequencing errors. Third, it provides the means to identify copies of the same molecule. This third requirement demands that one either employs a sufficient diversity of molecule identifier sequences and/or one makes sure one is confident that two sequencing reads with the same (start, end) breakpoint are derived from copies of the same molecule. The sampled portion of the fragmented molecules are utilized thus reduces the probability that >1 molecule has the same (start, end) breakpoint and/or molecule identifier sequence. This allows one to have confidence that a consensus is for a single fragment and prevents problems in the analysis. This problem is much more of a constraint when a very limited genomic region is sampled, as would be the case if analyzing a (typical) PCR amplicon. If one inadvertently groups reads containing a minority-variant with reads that contain the wild-type sequence then this could easily result in one inaccurately "correcting" the minority-variant to the wildtype sequence. FIG. 5 shows that using only a sampled portion of molecules after fragmentation, in effect executing a dilution step, before amplifying fragmented molecules results in more reads per group.

Figure 8:
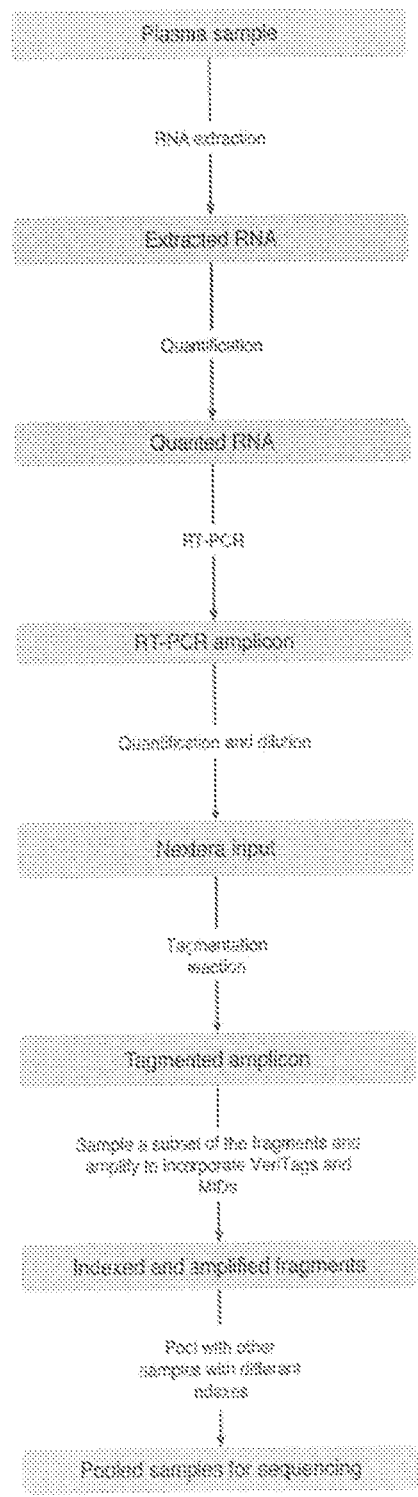
FIG. 8 shows an example of the entire workflow for the present method, from an initial plasma sample through pooled samples (assuming one desires to determine the sequence of multiple samples simultaneously and has labeled the samples individually with different indexes so as to enable such pooling).

In response to the challenges described above, a workflow called "VeX" has been developed that applies molecule identifier sequences to longer PCR amplicons and can be used over a large range of different viral titers. This workflow is outlined on the left side of FIG. 4 and described in more detail in FIGS. 7 and 8. Briefly, in an exemplary use of VeX workflow, viral RNA of known or unknown titer is extracted from blood plasma. A standard volume of RNA is input into an RT-PCR reaction. The resulting RT-PCR amplicon (which is longer than a typical sequence read on the sequence platform used later in the protocol) is then optionally quantitated and becomes the input to a process which will fragment the amplicons and then enable the appending of adaptors that are used later in the process. In one exemplary method, the fragmentation and attachment of adaptors can be done using transposon-based methods (Caruccio, Methods Mol Biol. 2011; 733:241-55) which performs both steps in a single reaction. Nextera XT (a kit commercially available from Illumina) is a transposon-based reaction that simultaneously fragments the RT-PCR amplicon and appends adaptors to the fragmented DNA (the "Tagmentation" step). It should be noted that alternative methods may be used for randomly fragmenting and appending adaptors, as explained in greater detail above and below. One exemplary method using Nextera XT employs 1 ng of the amplicon added to a Nextera XT tagmentation reaction. After tagmentation, a relatively small aliquot of the fragmented/tagged DNA is sampled, thereby imposing a mass bottleneck to strike the needed balance between sampling different molecules and getting sequence information from multiple copies of each molecule. The sampled fragments comprise the input for a modified PCR reaction which serves multiple purposes, among which are to (1) optionally fill-in the single-stranded 9-nt gap in the fragmented/tagged DNA (if the Nextera XT system is used); (2) add a molecule identifier sequence to each fragment (if the adaptors added earlier in the protocol did not contain such a sequence); (3) incorporate sequencing adaptors and sample identifiers and (4) generate multiple copies of the sampled fragments to make possible the generation of consensus sequences. Some of these steps are illustrated in FIG. 6 and FIG. 8, although, as described above and below, there are many ways to tag a sequence with a molecule identifier sequence and many ways to fragment a sample and add adaptors. Multiple viral RNA samples can thus be processed in parallel. Each sample is tagged with a different sample identifier sequence in the post-sampling PCR step. The resulting amplicons are pooled and sequenced on a single sequencing run. The sample identifiers are used to demultiplex sequencing reads to identify the originating sample.

As noted above and below, the initial example below using fragmentation with Nextera or Nextera XT is only one possible fragmentation and adaptor-appending method which can be employed in the VeX workflow. Other exemplary methods are discussed elsewhere in this application. Furthermore, also for the avoidance of doubt, the immediate example below uses viral RNA as a starting material for the entire process but in other situations the starting material from a virus or bacteria could be DNA and, if it is DNA, standard PCR would be employed as a first step rather than RT-PCR.

Quantitating the RT-PCR reaction and adding a known mass into the Nextera reaction helps to normalize reactions from RNA samples with different viral titers. Sampling the fragmented/tagged DNA after the Nextera reaction allows one to manipulate the relationship between the overall number of read groups and the average number of reads in each read group. The optimal sequencing run occurs when one has maximized the number of read groups that have sufficient reads to generate a consensus sequence. Unlike the conventional tagging methods, VeX does not tag the input molecule; rather, in VeX, the amplicon fragments are tagged, e.g., before or after the second amplification step of the workflow. Because the tagging is intentionally not done in the first step of the workflow, errors in the RT and first PCR reactions are not corrected but sequencing errors and late cycle errors in post-dilution PCR are largely corrected. In addition, sequencing errors from the second PCR can be used to estimate and 'correct' errors in the first PCR.

Amplification before fragmentation and adaptor-tagging, and then sampling after the fragmentation and tagging step are important to some embodiments of the VeX workflow. At first, it may naively appear that by limiting the number of molecules input into a fragmentation reaction, it might be possible to control and therefore limit the probability that >1 fragment has the same (start, end) breakpoint. After PCR and sequencing (assuming 100% efficiency) unique (start, end) breakpoints might then be used to reassemble the haplotype of each molecule. Further, multiple reads of the same fragment might be used to generate a consensus sequence, thereby reducing sequencing errors. In an exemplary use of this method to look at minority variants in HIV-1, one requires RT-PCR to make cDNA and to enrich viral sequences, and to take into account the wide dynamic range of viral molecules that may be present in any given sample. To detect minority-variants at ~1%, 100-1,000 amplicon molecules are input into the Nextera reaction. The Nextera reaction must therefore be highly efficient. Assuming that transposition is random, small fragments will be generated, which might not sequence efficiently or might be recalcitrant to mapping against the HIV-1 genome. In certain cases, reduced input mass into the Nextera reaction will tend to lead to shorter fragments because the ratio of enzyme to template is increased. One further complication of using Nextera is the directionality of Nextera insertion (50% of fragments do not have the correct sequence on both 5' and 3' ends). The conclusion is that, unfortunately, there is inherent inefficiency of the Nextera reaction (or alternative fragmentation methods) for small numbers of molecules. The VeX method has been carefully constructed to get around this inefficiency and address the other constraints discussed above. Furthermore, alternative fragmentation methods, as mentioned below, do not have all the limitations of Nextera and Nextera XT and may be preferred in certain applications.

The VeX method thus provides a workflow that addresses the essential requirements for a robust assay of minority variants in a viral or non-viral samples. VeX does not rely on highly efficient fragmentation and tagging; and small fragments and directionality of transposon insertion are not issues. Amplicons are fragmented and tagged with Nextera and (optionally) size selected. The library is then diluted to control the probability that >1 fragment has the same (start, end) breakpoint. The library is then amplified, for example, for 5-10 PCR cycles (32 to 1,024× amplification) before the sequencing chemistry is begun. During the subsequent analysis of the raw sequence data, consensus sequence is generated for fragments with the same (start, end) breakpoints. This corrects NGS and late PCR errors.

EXAMPLES

The application of next generation sequencing to diagnostics is complicated by noise introduced by errors and biases that occur in sample preparation and next generation sequencing (NGS). To demonstrate this complication, a 213 bp PCR amplicon was generated from *Escherichia coli* and the amplicon was sequenced on an Illumina MiSeq. Only paired-end read 1 was analyzed because these had better quality metrics than read 2 (as determined by FastQ analysis). 10,000 read 1 sequences that mapped to the known sequence were sampled before aligning reads to the reference and calculating base-to-base transition rates for base calls not expected in the reference sequence (i.e., errors). The mean error base-to-base transition rate was 0.11% but 10 calls had transition rates >3 standard deviations (sd) from the mean (>1.11%). A technical replicate had a similar mean base-to-base transition rate (0.12%), with 12 calls having transition rates >3 sd from the mean. Nine calls overlapped the two replicates, with one restricted to replicate 1 and two to replicate 2. These data indicate that both systematic and stochastic errors confound base-calling from ultradeep sequencing. These likely derive from sequence context and instrument bias (for example, Illumina data have historically demonstrated bias towards transversions because of insufficient discrimination of base emission spectra during imaging of the flow-cell). In addition, results depend on the overall quality of the sequencing reads. In this case, the read 2 paired-end read had significantly more noise than read 1 (data not shown). The presence of such systematic and stochastic errors in conventional ultradeep sequencing represents one of the many reasons why the VeX workflow was developed.

Example 1

The performance of the VeX workflow was demonstrated using primers to create RT-PCR amplicons covering HIV-1 vif, vpr, and vpu generated from National Institute for Biological Standards HIV-1 Genotype panel (see Gall et al 2012). Amplicons were mixed at 99:1 from subtypes A:C, C:D and D:A (A [US1190], C [AF286235] and D [U88824]). 1 ng of each synthetic mix was added to a Nextera XT reaction. For purposes further explained below (and not necessary for routine use of the workflow), after the fragmenting/tagging step, reactions were serially diluted between 10× and $10^7$×. The diluted Nextera reactions were amplified with indexed primers before pooling and sequencing on the Illumina MiSeq, a commercially available next generation DNA sequencing platform. After sequencing, the reads were grouped by their fragmentation breakpoints and consensus sequences were generated for each read group. See FIG. 7 for the analysis approach that was performed on a computer programmed to execute these steps. Consensus sequences were then partitioned into separate bins based on their most likely HIV subtype. To determine the most likely subtype, each consensus read was split into overlapping kmers (including forward and reverse complement strands) and compared to kmers derived from each HIV-1 subtype (including only the forward strand) generated from 2,233 sequences in the Los Alamos HIV web alignment.

The most likely subtype was defined as the subtype with the most kmers in common with either the forward, or reverse complement, of the consensus sequence. This step also orientated the consensus sequence relative to the HIV-1 genome. Consensus reads for each subtype were then processed separately using an inchworm algorithm (Grabherr et al 2011) to de novo assemble contigs. Inchworm constructs linear contigs by (1) constructing a kmer dictionary from all consensus sequence reads; (2) selecting the most frequent kmer in the dictionary to seed a contig assembly; (3) extending the seed in each direction by finding the highest occurring kmer with a k−1 overlap with the current contig terminus and concatenating its terminal base to the growing contig sequence (once a kmer has been used it is removed from the dictionary), (4) extending the sequence in either direction until it cannot be extended further, then reporting the contig, (5) repeating steps 2-4 until the entire kmer dictionary has been exhausted. Contigs with length <500 nts were discarded.

Example 2

Figure 9:
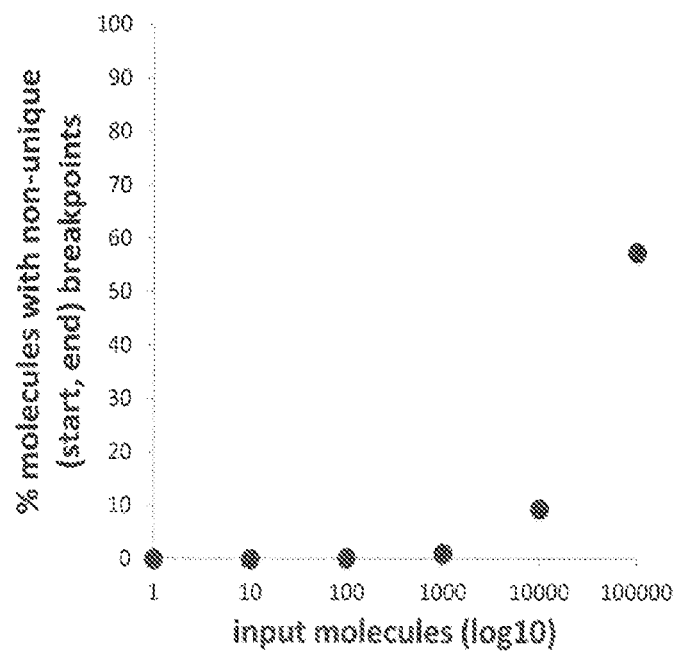
FIG. 9 is a graph showing the percentage of fragments generated that have the same breakpoints when different numbers of copies of a 4 kb input molecule are fragmented.
Figure 10:
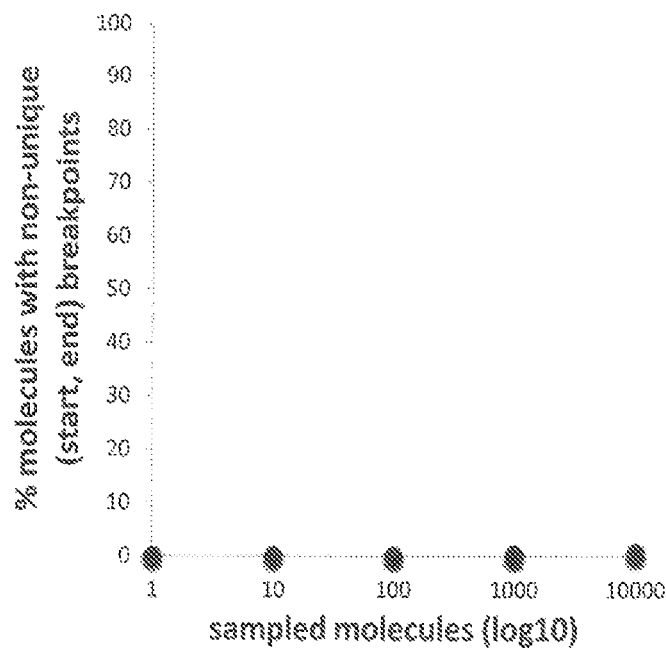
FIG. 10 is a graph that shows the percentage of fragments with the same breakpoints when different numbers of fragments are sampled from an initial pool generated from 100,000 copies of a randomly fragmented 4 kb amplicon.

A computer model was developed to investigate how the mass bottlenecks affect the probability that >1 molecule shares the same (start, end) breakpoints, assuming a 4 kb amplicon, with each base having a 1/200 chance of being the site of transposon insertion. After stochastically generating breakpoints, fragments that were too small (<50 bp), or too large (>1,000 bp) were discarded. The number of fragments with the same (start, end) coordinate to the total number of fragments were then compared. The simulations were repeated for 10 iterations, for different numbers of input molecules. FIG. 9 demonstrates that, as expected, the probability that >1 molecule has the same (start, end) breakpoint increases with the number of input molecules. Next, the model was extended by randomly sampling molecules after fragmentation and without replacement. Assuming 100,000 input molecules, which yields ~57% duplicates without sampling and approximately 1.9 million fragments of the correct size. FIG. 10 shows that sampling a limited number of molecules after fragmentation significantly reduces the probability that >1 molecule has the same (start, end) breakpoint. Note that 10,000 sampled molecules is an ~190× dilution from the number of fragments generated from 100,000 input molecules; and that the x-axes of FIG. 9 and FIG. 10 are not directly comparable (FIG. 9 is input molecules; FIG. 10 is sampled molecules).

Example 3

FIG. 8 is a flowchart of the entire workflow when Nextera fragmentation is employed. The RNA extraction is typically done with a Qiagen Viral RNA extraction kit, such as the QIAamp Ultrasens Virus Kit, using a sample volume of up to 1 mL or a QiAamp Viral RNA Mini Kit using a sample volume of up to 140 µL. In both cases, the elution volume is up to 60 µL Illumina's Tagmentation reaction (the reaction employing Nextera to fragment the amplicons) uses 10 µL of Tagment DNA buffer with 5 µL of amplicon diluted to 0.2 ng/µL and 5 µL of Amplicon Tagment Mix to give a total volume of 20 µL. This is incubated at 55° C. for 5 min and then the temperature is reduced to 10°C. As soon as the reaction reaches 10°C, 5 µL of Neutralize Tagment buffer is added.

The second PCR, which adds MIDs and molecule identifier sequences (VeriTags), uses these conditions: 5× Phusion HF buffer (NEB) 5 µL, 10 mM dNTPs 0.5 µL, 10 µM Nextera i5 indexing primer 1.25 µL, 500 nM 3'-blocked VeriTag oligo 0.25 µL, 10 µM reverse amplification primer 1.25 µL, 2 U/µL Phusion High Fidelity DNA Polymerase or Phusion Hot Start Flex DNA Polymerase (both NEB) 0.25 µL, water 4.25 µL diluted Nextera reaction for a total of 12.75 µL.

The PCR cycling conditions used are as follows:

72° C. for 3 min 98° C. for 30 sec then 2 cycles of: 98° C. for 10 sec 58° C. for 30 sec 72° C. for 30 sec then (<30) cycles of: 98° C. for 10 sec, and 72° C. for 60 sec, followed by 72° C. for 5 min, then 4° C. hold.

Exemplary Embodiments

The RT-PCR step could eventually be integrated with a real-time qPCR to simultaneously monitor titer when the application is to sequence variants of RNA viruses such as HIV and HCV where the titer is important and highly variable.

Listed below in this section are several alternative implementations of certain of the steps (a) through (j) listed above in the Summary section of this document:

Amplification Methods for Step (a):
Where such amplification product of (a) is a PCR product
Where the first nucleic acid sample of (a) is quantified
Where such amplification product of (a) is quantified
Where such amplification product of (a) results from RT-PCR from an RNA sample
Where such amplification product of (a) results from PCR from a DNA sample
Where such RNA or DNA is from a virus
Where such virus is HIV or HCV
Where such amplification product could be produced from multiple regions of a particular genome, e.g., to capture all the coding regions of an HIV or HCV genome.

Fragmenting Methods for Step (b):
Where the random fragmenting is done by a transposon system
Where the random fragmenting is done by ultrasonic disruption
Where the random fragmenting is done by enzymatic methods
Where the random fragmenting is done by mechanical methods such as shearing in a turbulent fluid, grinding, etc.

Adaptor Appending Methods for Step (c):
Where the adaptors are attached to the fragmented molecules by a transposon system (See, e.g., Nextera or Nextera XT product information) or by ligation reactions such as described, by reference, in U.S. Pat. No. 8,029,993. Such adaptors could also comprise an index or MID region that enables one to distinguish one sample from another. [Adaptors could also be single-stranded i.e. ssDNA ligations, or hairpins etc.]

Amplification Methods for Step (d):
Where the amplification of (d) includes a primer with an index region comprising an MID that enables one to distinguish one sample from another
Where a second sample corresponding to an index region comprising an MID different from that of the first sample is processed identically through the workflow until the pooling step is executed, e.g., as shown in FIG. 8.
Where the amplified regions of step (d) performed on the first sample are pooled with the amplified regions of step (d) performed on the second sample.

Sequencing Analysis Methods for Step (e to h):
Where the sequences analyzed in steps (e) through (h) are first grouped by their MID so that the resulting analysis is specific for the sample identified by such an MID.
Where the amplification of (d) includes, in addition to two adaptor-specific standard PCR primers, a primer or a 3'-blocked oligonucleotide (e.g. an inverted dA residue that prevents extension of the oligonucleotide by a polymerase) that contains a molecule identifier sequence region where such molecule identifier sequence region is randomly chosen from a set of unique sequences. In certain cases the thermal cycling protocol is not a standard PCR. For example, the oligonucleotide containing the molecule identifier sequence may be designed to have a lower annealing temperature than the standard primers. The first one or two cycles of the PCR may be performed at a lower annealing temperature (e.g. 55° C.) that facilitates incorporation of the molecule identifier sequence into the products generated by the polymerase. The remaining cycles may then be performed at a higher annealing temperature (e.g. 72° C.) that prevents or limits further molecule identifier sequence incorporation but that allows amplification by the standard PCR primers. See FIG. 6 for additional details.

Software Grouping Methods for Step (f):
Where the grouping in (f) is done or assisted by reference to the identity of the molecule identifier sequence (VeriTag) region of the determined sequence of a particular sequence read.
Where the grouping in (f) is done by reference to the genomic sequence regions adjacent to the adaptor-attached sequences.
Where the grouping in (f) is done by reference to both the genomic sequence regions adjacent to the adaptor-attached sequences and by reference to the identity of the molecule identifier sequence (VeriTag) region of the determined sequence of a particular sequence read.

In one exemplary method, sequencing is performed using paired-end reads. Read 1 and read 2 prefixes are recovered and reads are grouped if they have the same sequence. In this example, the read 1 and read 2 sequences are both 5' to 3'. The prefix is simply the start of the read i.e. splitting the read into a prefix, infix and suffix. In one example, the read might start with 8 nucleotides from the VeriTag sequence, then 4 nucleotides from the overhang used for ligation, then read into HIV-1. If bases are numbered from 0, 1, 2, etc. then bases 12-42 would be the 30 nt prefix sequence. The read 1 and read 2 prefixes might contain errors. Therefore grouping of sequencing reads with non-identical prefix sequences can be performed. In one example, prefixes are length 30 nt and a Hamming distance of 2 between prefixes is allowed so that small mismatches can be recovered. In other words, more than 2 bases must change for one prefix to convert into another.

One issue with using prefixes/Hamming distances is that reads must have the same breakpoints. If there are sequencing miscalls at the read 5' end or in the adaptor sequence then in one exemplary process utilizing Illumina NGS methods the Illumina trimmer software (which is used to remove aberrant base incorporations) can inadvertently remove some of the read bases. This has the effect of making some reads that probably derive from copies of the same input molecule have different start, ends. This can largely be resolved using a combination of a molecule identifier sequence (VeriTag) and breakpoints. First, the reads are demultiplexed using the molecule identifier sequence (VeriTag). Then reads with similar breakpoints are computationally grouped. This can also be achieved using similarity metrics that allow insertions/deletions such as the Levenshtein edit distance.

In certain applications where there is sufficient starting template and the template is of low sequence complexity, the amplification step a) may be omitted.

What is claimed is:

1. A method of evaluating a sequence variation in a sample, comprising:
   a) amplifying a nucleic acid product from an initial sample;
   b) fragmenting an amount of the amplified nucleic acid product produced by step a) to produce linear nucleic acid fragments with random fragmentation breakpoints;
   c) attaching, by ligation or by primer extension, an adaptor to each random fragmentation breakpoint of the fragments produced in step b) to produce linear adaptor-tagged nucleic acid fragments;
   d) obtaining a random sample of no more than 10% of the product of step c) and amplifying the linear adaptor-tagged nucleic acid fragments contained in the random sample using one or more primers that hybridize to the adaptor to produce copies of the fragments;
   e) sequencing at least some of the copies of the fragments produced in step d) to produce a plurality of sequence reads;
   f) computationally grouping the sequence reads of step e), wherein the grouping provides a plurality of read groups each read group comprising fragments that have the same fragmentation breakpoints and substantially identical sequences;
   g) deriving a consensus sequence for each of the read groups provided by step f);
   h) aligning the consensus sequences derived by step g) with a reference sequence; and
   i) identifying a position in the alignment that comprises a sequence variation.

2. The method of claim 1, further comprising estimating the abundance of the sequence variation in the sample.

3. The method of claim 1, wherein the method further comprises:
   at a position corresponding to a sequence variation, counting:
   i. the number of consensus sequences that comprise the sequence variation; and
   ii. the number of consensus sequences that do not comprise the sequence variation or the total number of consensus sequences.

4. The method of claim 3, further comprising determining whether the sequence variation is present in the sample and/or estimating the abundance of the sequence variation in the sample using the numbers counted in i. and ii.

5. The method of claim 4, wherein the determining and/or estimating uses an error model.

6. The method of claim 3, wherein the method further comprises determining whether said sequence variant is in the sample, wherein a higher number of consensus sequences for the sequence variant relative to the number of consensus sequences that do not comprise the sequence variation or the total number of consensus sequences that comprise the position of the sequence variation increases the confidence of the determination.

7. The method of claim 3, wherein the method further comprises estimating the amount of the sequence variant in the sample, wherein a higher number of consensus sequences for the sequence variant relative to the number of consensus sequences that do not comprise the sequence variation or the total number of consensus sequences that comprise the position of the sequence variation correlates with the abundance of the sequence variant in the sample.

8. The method of claim 1, wherein the amplified nucleic acid produced in step a) is in the range of 100 bp to 50 kb in length.

9. The method of claim 1, wherein the nucleic acid product amplified from the initial sample in step a) comprises a segment of a viral or bacterial genome.

10. The method of claim 1, wherein the nucleic acid product amplified from the initial sample in step a) comprises a segment of a mammalian or mitochondrial genome.

11. The method of claim 1, wherein the sequence variation is present at a copy number of less than 1 in 20, relative to other molecules that do not contain the sequence variation, in the product produced by step a).

12. The method of claim 1, wherein the amplifying of step a) is done by PCR or RT-PCR.

13. The method of claim 1, wherein the fragmenting step b) is done using physical, chemical, or enzymatic means or using transposable elements.

14. The method of claim 1, wherein the average size of the fragments produced in step b) is in the range of 100-700 nucleotides in length.

15. The method of claim 1, wherein the amplifying step d) comprises 5-40 cycles of PCR.

16. The method of claim 1, wherein the random sample: used in step d) is less than 1/100th of the product of step c).

17. The method of claim 1, wherein the amplifying step d) results in amplification of less than 1 in 1,000 of the fragments produced in step b).

18. The method of claim 1, wherein the method comprises adding a molecule identifier sequence to the fragments prior to or in step c), and wherein the grouping step f) is done by identifying which sequence reads have the same end sequences and the same molecule identifier sequence.

19. The method of claim 1, wherein the initial sample contains an unknown amount of initial template molecules.

20. The method of claim 1, wherein the read groups are defined by paired-end reads.

21. The method of claim 1, wherein the amplifying step d) comprises appending a sample identifier sequence to the amplified fragments.

* * * * *